(12) United States Patent
Flatt et al.

(10) Patent No.: US 10,357,324 B2
(45) Date of Patent: Jul. 23, 2019

(54) STERILE BARRIER ASSEMBLY, MOUNTING SYSTEM, AND METHOD FOR COUPLING SURGICAL COMPONENTS

(71) Applicant: Stryker Corporation, Kalamazoo, MI (US)

(72) Inventors: James E. Flatt, Kalamazoo, MI (US); Douglas A. Staunton, Kalamazoo, MI (US); Matthew B. Pastrick, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 544 days.

(21) Appl. No.: 15/048,232

(22) Filed: Feb. 19, 2016

(65) Prior Publication Data

US 2016/0242861 A1 Aug. 25, 2016

Related U.S. Application Data

(60) Provisional application No. 62/118,737, filed on Feb. 20, 2015.

(51) Int. Cl.

| A61B 46/00 | (2016.01) |
|---|---|
| A61B 46/10 | (2016.01) |
| A61B 34/30 | (2016.01) |
| A61B 90/50 | (2016.01) |
| A61B 34/00 | (2016.01) |
| A61B 90/40 | (2016.01) |
| A61B 17/00 | (2006.01) |

(52) U.S. Cl.
CPC .............. *A61B 46/10* (2016.02); *A61B 34/30* (2016.02); *A61B 34/70* (2016.02); *A61B 90/40* (2016.02); *A61B 90/50* (2016.02); *A61B 2017/00477* (2013.01)

(58) Field of Classification Search
CPC ......... A61B 34/30; A61B 34/70; A61B 90/40; A61B 90/50; A61B 46/10; A61B 2019/085; A61B 2019/086; A61B 2019/106; A61B 19/087
See application file for complete search history.

(56) References Cited

U.S. PATENT DOCUMENTS

| 3,482,567 A | 12/1969 | Franklin |
|---|---|---|
| 3,483,494 A | 12/1969 | Cromie |

(Continued)

FOREIGN PATENT DOCUMENTS

| AU | 754882 B2 | 11/2002 |
|---|---|---|
| GB | 2483154 A | 2/2012 |

(Continued)

OTHER PUBLICATIONS

International Search Report and Written Opinion for International Application No. PCT/US2016/018691 dated Jun. 1, 2016.

(Continued)

*Primary Examiner* — Ophelia A Hawthorne
(74) *Attorney, Agent, or Firm* — Howard & Howard Attorneys PLLC

(57) ABSTRACT

A sterile barrier assembly, mounting system, and method for kinematically coupling first and second surgical components together through the sterile barrier assembly so that positioning is repeatable and deterministic.

31 Claims, 27 Drawing Sheets

(56) References Cited

U.S. PATENT DOCUMENTS

| | | |
|---|---|---|
| 3,796,477 A | 3/1974 | Geraci |
| 4,409,738 A | 10/1983 | Renander et al. |
| 4,522,196 A | 6/1985 | Cunningham et al. |
| 4,770,497 A | 9/1988 | Brown |
| 5,042,981 A | 8/1991 | Gross |
| 5,080,108 A | 1/1992 | Roth |
| 5,122,904 A | 6/1992 | Fujiwara et al. |
| 5,184,601 A | 2/1993 | Putman |
| 5,274,500 A | 12/1993 | Dunn |
| 5,413,573 A | 5/1995 | Koivukangas |
| 5,433,221 A | 7/1995 | Adair |
| 5,441,042 A | 8/1995 | Putman |
| 5,457,962 A | 10/1995 | Faries, Jr. et al. |
| 5,467,223 A | 11/1995 | Cleveland, Jr. et al. |
| 5,524,643 A | 6/1996 | Faries, Jr. et al. |
| 5,574,561 A | 11/1996 | Boudreau et al. |
| 5,591,119 A | 1/1997 | Adair |
| 5,626,216 A | 5/1997 | Sperling et al. |
| 5,642,956 A | 7/1997 | Hale |
| 5,669,152 A | 9/1997 | McMurtry |
| 5,762,458 A | 6/1998 | Wang et al. |
| 5,769,554 A | 6/1998 | Slocum |
| 5,785,643 A | 7/1998 | Lynn |
| 5,800,483 A | 9/1998 | Vought |
| 5,816,252 A | 10/1998 | Faries, Jr. et al. |
| 5,853,363 A | 12/1998 | Vought |
| 5,855,583 A | 1/1999 | Wang et al. |
| 5,857,467 A | 1/1999 | Faries, Jr. et al. |
| 5,876,328 A | 3/1999 | Fox et al. |
| 5,891,020 A | 4/1999 | Luber et al. |
| 5,960,794 A | 10/1999 | Shaw |
| 6,050,981 A | 4/2000 | Lampropoulos et al. |
| 6,063,095 A | 5/2000 | Wang et al. |
| 6,065,898 A | 5/2000 | Hale |
| 6,072,569 A | 6/2000 | Bowen |
| 6,102,044 A | 8/2000 | Naidyhorski |
| 6,102,850 A | 8/2000 | Wang et al. |
| 6,116,966 A | 9/2000 | Little et al. |
| 6,132,368 A | 10/2000 | Cooper |
| 6,228,089 B1 | 5/2001 | Wahrburg |
| 6,325,351 B1 | 12/2001 | Hale et al. |
| 6,330,837 B1 | 12/2001 | Charles et al. |
| 6,331,181 B1 | 12/2001 | Tierney et al. |
| 6,346,072 B1 | 2/2002 | Cooper |
| 6,357,445 B1 | 3/2002 | Shaw |
| 6,371,121 B1 | 4/2002 | Faries, Jr. et al. |
| 6,375,610 B2 | 4/2002 | Verschuur |
| 6,431,530 B1 | 8/2002 | Stamps et al. |
| 6,436,107 B1 | 8/2002 | Wang et al. |
| 6,460,436 B1 | 10/2002 | Salzer et al. |
| 6,471,172 B1 | 10/2002 | Lemke et al. |
| 6,491,612 B1 | 12/2002 | Kurup et al. |
| 6,491,701 B2 | 12/2002 | Tierney et al. |
| 6,533,594 B1 | 3/2003 | Kurup |
| 6,612,310 B2 | 9/2003 | Sklar |
| 6,661,955 B1 | 12/2003 | Calvet et al. |
| 6,699,177 B1 | 3/2004 | Wang et al. |
| 6,720,988 B1 | 4/2004 | Gere et al. |
| 6,755,195 B1 | 6/2004 | Lemke et al. |
| 6,804,547 B2 | 10/2004 | Pelzer et al. |
| 6,805,453 B2 | 10/2004 | Spetzler et al. |
| 6,810,881 B2 | 11/2004 | Faries, Jr. et al. |
| 6,840,895 B2 | 1/2005 | Perry et al. |
| 6,843,252 B2 | 1/2005 | Harrison et al. |
| 6,860,271 B2 | 3/2005 | Faries, Jr. et al. |
| 6,863,071 B2 | 3/2005 | Annett et al. |
| 6,866,671 B2 | 3/2005 | Tierney et al. |
| 6,910,485 B2 | 6/2005 | Faries, Jr. et al. |
| 6,918,395 B2 | 7/2005 | Faries, Jr. et al. |
| 6,945,814 B2 | 9/2005 | Snape et al. |
| 7,002,102 B2 | 2/2006 | Münch et al. |
| 7,027,893 B2 | 4/2006 | Perry et al. |
| 7,048,745 B2 | 5/2006 | Tierney et al. |
| 7,118,582 B1 | 10/2006 | Wang et al. |
| 7,122,032 B2 | 10/2006 | Shinmura et al. |
| 7,137,763 B2 | 11/2006 | Lawson |
| 7,252,453 B1 | 8/2007 | Little |
| 7,328,086 B2 | 2/2008 | Perry et al. |
| 7,331,967 B2 | 2/2008 | Lee et al. |
| 7,347,210 B2 | 3/2008 | Faries, Jr. et al. |
| 7,350,373 B1 | 4/2008 | Faries, Jr. et al. |
| 7,357,774 B2 | 4/2008 | Cooper |
| 7,418,966 B2 | 9/2008 | Faries, Jr. et al. |
| 7,524,320 B2 | 4/2009 | Tierney et al. |
| 7,666,191 B2 | 2/2010 | Orban, III et al. |
| 7,699,855 B2 | 4/2010 | Anderson et al. |
| 7,727,244 B2 | 6/2010 | Orban, III et al. |
| 7,789,874 B2 | 9/2010 | Yu et al. |
| 7,819,885 B2 | 10/2010 | Cooper |
| 7,850,642 B2 | 12/2010 | Moll et al. |
| 7,886,743 B2 | 2/2011 | Cooper et al. |
| 7,947,050 B2 | 5/2011 | Lee et al. |
| 7,947,051 B2 | 5/2011 | Lee et al. |
| 7,955,322 B2 | 6/2011 | Devengenzo et al. |
| 7,959,860 B2 | 6/2011 | Faries, Jr. et al. |
| 7,963,288 B2 | 6/2011 | Rosenberg et al. |
| 7,963,913 B2 | 6/2011 | Devengenzo et al. |
| 7,972,298 B2 | 7/2011 | Wallace et al. |
| 7,974,681 B2 | 7/2011 | Wallace et al. |
| 8,005,537 B2 | 8/2011 | Hlavka et al. |
| 8,005,570 B2 | 8/2011 | Gloden et al. |
| 8,021,326 B2 | 9/2011 | Moll et al. |
| 8,052,636 B2 | 11/2011 | Moll et al. |
| 8,054,184 B2 | 11/2011 | Cline et al. |
| 8,074,657 B2 | 12/2011 | Scott et al. |
| 8,105,319 B2 | 1/2012 | Doyle et al. |
| 8,105,338 B2 | 1/2012 | Anderson et al. |
| 8,132,816 B2 | 3/2012 | Norton et al. |
| 8,142,447 B2 | 3/2012 | Cooper et al. |
| 8,148,666 B2 | 4/2012 | Faries, Jr. et al. |
| 8,182,469 B2 | 5/2012 | Anderson et al. |
| 8,182,470 B2 | 5/2012 | Devengenzo et al. |
| 8,190,238 B2 | 5/2012 | Moll et al. |
| 8,202,278 B2 | 6/2012 | Orban, III et al. |
| 8,206,053 B2 | 6/2012 | Bennett et al. |
| 8,206,406 B2 | 6/2012 | Orban, III |
| 8,209,840 B2 | 7/2012 | Norton |
| 8,216,250 B2 | 7/2012 | Orban, III et al. |
| 8,220,468 B2 | 7/2012 | Cooper et al. |
| 8,241,208 B2 | 8/2012 | Jiang et al. |
| 8,257,303 B2 | 9/2012 | Moll et al. |
| 8,264,767 B2 | 9/2012 | Nozawa |
| 8,273,076 B2 | 9/2012 | Devengenzo et al. |
| 8,311,626 B2 | 11/2012 | Hlavka et al. |
| 8,375,808 B2 | 2/2013 | Blumenkranz et al. |
| 8,394,054 B2 | 3/2013 | Wallace et al. |
| 8,409,136 B2 | 4/2013 | Wallace et al. |
| 8,413,948 B2 | 4/2013 | Kemeny |
| 8,460,277 B2 | 6/2013 | Suarez et al. |
| 8,500,132 B2 | 8/2013 | Norton |
| 8,529,582 B2 | 9/2013 | Devengenzo et al. |
| 8,533,930 B2 | 9/2013 | Norton |
| 8,548,779 B2 | 10/2013 | Ortmaier et al. |
| 8,601,667 B2 | 12/2013 | Norton |
| 8,602,031 B2 | 12/2013 | Reis et al. |
| 8,608,773 B2 | 12/2013 | Tierney et al. |
| 8,672,922 B2 | 3/2014 | Loh et al. |
| 8,720,448 B2 | 5/2014 | Reis et al. |
| 8,740,881 B2 | 6/2014 | Ortmaier et al. |
| 8,746,252 B2 | 6/2014 | McGrogan et al. |
| 8,747,288 B2 | 6/2014 | Strotzer et al. |
| 8,784,435 B2 | 7/2014 | Cooper et al. |
| 8,794,993 B2 | 8/2014 | Norton |
| 8,857,821 B2 | 10/2014 | Norton et al. |
| 8,910,637 B2 | 12/2014 | Winer |
| 8,945,095 B2 | 2/2015 | Blumenkranz et al. |
| 8,998,930 B2 | 4/2015 | Orban, III |
| 9,096,033 B2 | 8/2015 | Holop et al. |
| RE45,681 E | 9/2015 | Perry et al. |
| 9,254,572 B2 | 2/2016 | Strotzer |
| 9,724,830 B2 | 8/2017 | Norton et al. |
| 9,731,392 B2 | 8/2017 | Takla et al. |
| 10,047,908 B1 | 8/2018 | Bohle, II et al. |
| 2002/0137358 A1 | 9/2002 | Binnard et al. |

(56) References Cited

U.S. PATENT DOCUMENTS

| | | |
|---|---|---|
| 2006/0100610 A1 | 5/2006 | Wallace et al. |
| 2006/0161138 A1* | 7/2006 | Orban, III ............ B25J 19/0075 606/1 |
| 2006/0191540 A1 | 8/2006 | Lamprich et al. |
| 2007/0282311 A1 | 12/2007 | Scott et al. |
| 2008/0147089 A1 | 6/2008 | Loh et al. |
| 2008/0218770 A1 | 9/2008 | Moll et al. |
| 2008/0236598 A1 | 10/2008 | Gobel |
| 2009/0088772 A1 | 4/2009 | Blumenkranz |
| 2009/0248039 A1 | 10/2009 | Cooper et al. |
| 2010/0009825 A1 | 1/2010 | Norton et al. |
| 2010/0065068 A1 | 3/2010 | Hamazaki et al. |
| 2010/0170519 A1 | 7/2010 | Romo et al. |
| 2010/0241137 A1 | 9/2010 | Doyle et al. |
| 2010/0268249 A1 | 10/2010 | Stuart |
| 2010/0268250 A1 | 10/2010 | Stuart et al. |
| 2010/0308195 A1 | 12/2010 | Yu et al. |
| 2011/0087238 A1 | 4/2011 | Wang et al. |
| 2011/0088702 A1 | 4/2011 | King et al. |
| 2011/0190790 A1 | 8/2011 | Summerer et al. |
| 2011/0213383 A1 | 9/2011 | Lee et al. |
| 2011/0238083 A1 | 9/2011 | Moll et al. |
| 2011/0277775 A1 | 11/2011 | Holop et al. |
| 2011/0277776 A1 | 11/2011 | McGrogan et al. |
| 2012/0065472 A1 | 3/2012 | Doyle et al. |
| 2012/0071752 A1 | 3/2012 | Sewell et al. |
| 2012/0071821 A1 | 3/2012 | Yu |
| 2012/0071822 A1 | 3/2012 | Romo et al. |
| 2012/0071894 A1 | 3/2012 | Tanner et al. |
| 2012/0071895 A1 | 3/2012 | Stahler et al. |
| 2012/0080040 A1 | 4/2012 | Skora et al. |
| 2012/0080041 A1 | 4/2012 | Skora et al. |
| 2012/0083799 A1 | 4/2012 | Chen et al. |
| 2012/0083825 A1 | 4/2012 | Stroup et al. |
| 2012/0191107 A1 | 7/2012 | Tanner et al. |
| 2012/0209174 A1 | 8/2012 | Moll et al. |
| 2012/0209291 A1 | 8/2012 | Anderson et al. |
| 2012/0232566 A1 | 9/2012 | Orban, III et al. |
| 2012/0239060 A1 | 9/2012 | Orban, III |
| 2012/0247489 A1 | 10/2012 | Orban, III et al. |
| 2012/0289974 A1 | 11/2012 | Rogers et al. |
| 2012/0312308 A1 | 12/2012 | Allen |
| 2013/0035537 A1 | 2/2013 | Wallace et al. |
| 2013/0092177 A1 | 4/2013 | Chua et al. |
| 2013/0174858 A1 | 7/2013 | Annett |
| 2013/0211401 A1 | 8/2013 | Bailey et al. |
| 2013/0231679 A1 | 9/2013 | Wallace et al. |
| 2013/0247921 A1 | 9/2013 | Dye et al. |
| 2013/0331858 A1 | 12/2013 | Devengenzo et al. |
| 2014/0039681 A1 | 2/2014 | Bowling et al. |
| 2014/0171965 A1 | 6/2014 | Loh et al. |
| 2014/0326254 A1 | 11/2014 | McGrogan et al. |
| 2015/0047647 A1 | 2/2015 | Winer |
| 2015/0073437 A1 | 3/2015 | Devengenzo et al. |
| 2015/0133960 A1 | 5/2015 | Lohmeier et al. |
| 2015/0142012 A1 | 5/2015 | Lohmeier et al. |
| 2015/0148817 A1 | 5/2015 | Lohmeier et al. |
| 2015/0148818 A1 | 5/2015 | Lohmeier et al. |
| 2015/0150638 A1 | 6/2015 | Lohmeier et al. |
| 2015/0173841 A1 | 6/2015 | Orban |
| 2015/0202009 A1 | 7/2015 | Nussbaumer et al. |
| 2016/0039059 A1 | 2/2016 | Takla et al. |
| 2016/0052146 A1 | 2/2016 | Berrocal et al. |
| 2016/0059424 A1 | 3/2016 | Zachary et al. |
| 2018/0304475 A1 | 10/2018 | Zachary et al. |
| 2018/0316139 A1 | 11/2018 | Berrocal et al. |

FOREIGN PATENT DOCUMENTS

| | | |
|---|---|---|
| WO | 2009092701 A1 | 7/2009 |
| WO | 2009123891 A1 | 10/2009 |
| WO | 20090123925 A1 | 10/2009 |
| WO | 2010121107 A1 | 10/2010 |
| WO | 2010121117 A1 | 10/2010 |
| WO | 2013075204 A1 | 5/2013 |
| WO | 2013075205 A1 | 5/2013 |
| WO | 20130159932 A1 | 10/2013 |
| WO | 2014162217 A1 | 10/2014 |
| WO | 2014165828 A1 | 10/2014 |
| WO | 2015052629 A1 | 4/2015 |
| WO | 20150110542 A1 | 7/2015 |

OTHER PUBLICATIONS

"Design of Low-Cost Kinematic Couplings Using Formed Balls and Grooves in Sheet Metal Parts" by Martin L. Culpepper, Alexander Slocum and Peter Bailey (Massachusetts Institute of Technology, Cambridge, MA), Oct. 2003, 4 pages.

"Adjustable Mirror Mount Design Using Kinematic Principles" by D.A. Bateman, Dip. Tech.—Royal Aircraft Establishment—Technical Report No. 66349, Nov. 1966. U.D.C. No. 621.3-21: 531.1: 681.4. 28 pages.

Precision Engineering Journal of the International Societies for Precision Engineering and Nanotechnology 25 (2001) 114-127— "Optimal design techniques for kinematic couplings" by Layton C. Hale, Lawrence Livermore National Laboratory, Livermore, CA, USA; Alexander H. Slocum, Department of Mechanical Engineering, Massachusetts Institute of Technology, Cambridge, MA, USA. Oct. 5, 2000. 14 pages.

Instrument Science and Technology "Kinematic design of fine mechanisms in instruments" by J.E. Furse, Engineering Services, National Physical Laboratory, Teddington, Middlesex, UK. J. Phys. E: Sci. Instrum., vol. 14, 1981. Printed in Great Britain. 8 pages.

"Design of three-grove kinematic couplings" by Alexander H. Slocum, Department of Mechanical Engineering, Massachusetts Institute of Technology, Cambridge, MA, USA. 1992 Butterworth-Heinemann. 10 pages.

Machine-assisted English language translation for WO2009092701 (A1) extracted from Espacenet.com on Aug. 2, 2016, 11 pages.

Machine-assisted English language translation for WO2013159932 (A1) extracted from Espacenet.com on Aug. 2, 2016, 12 pages.

* cited by examiner

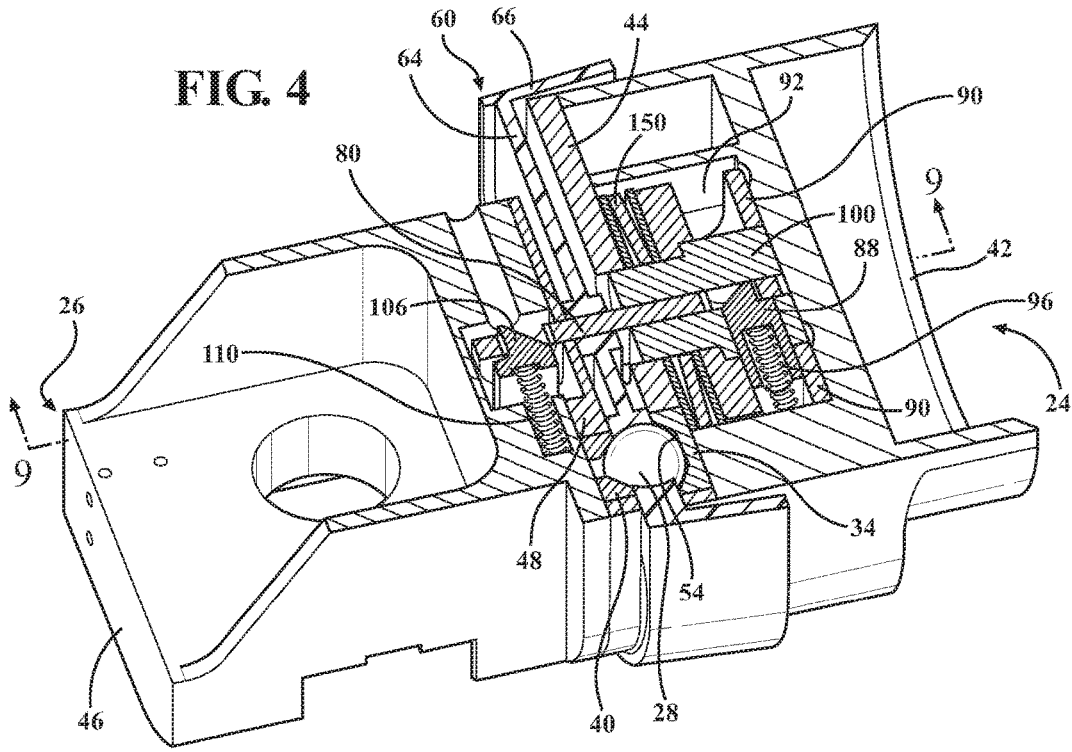
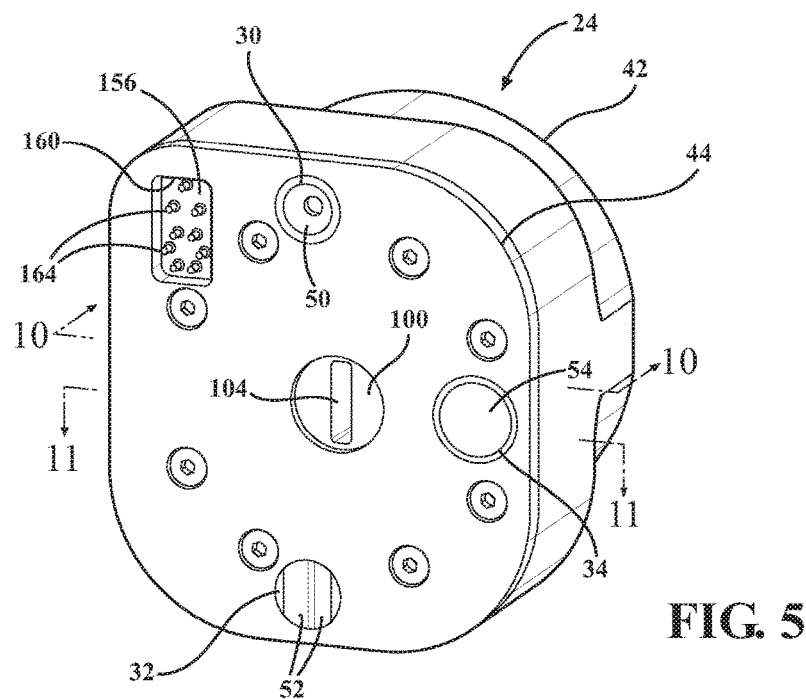

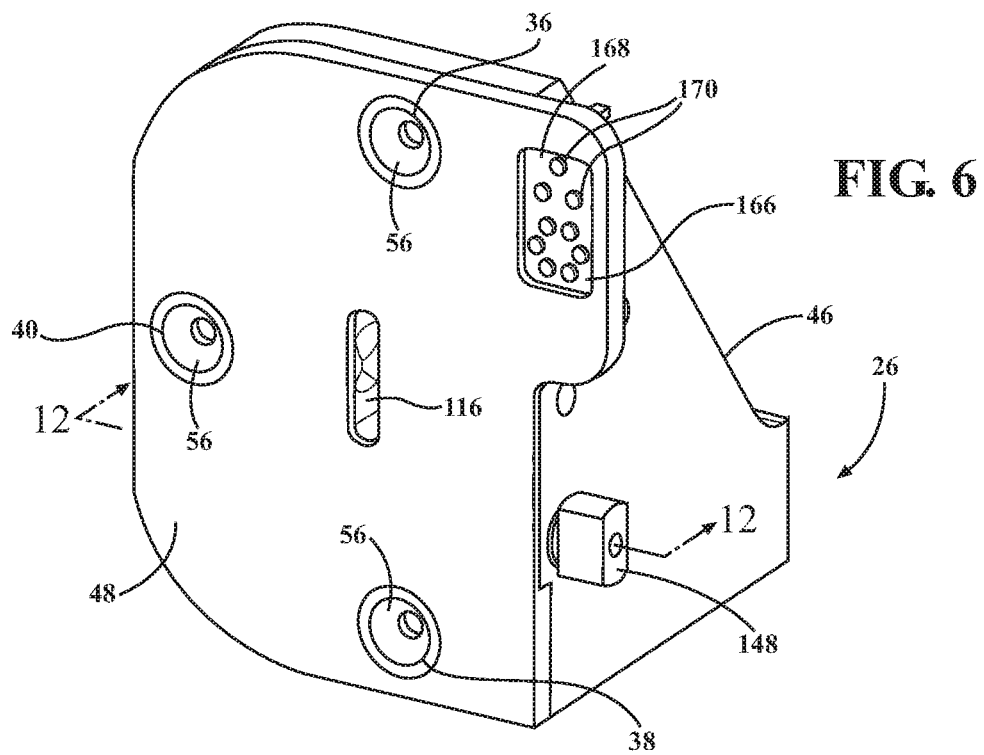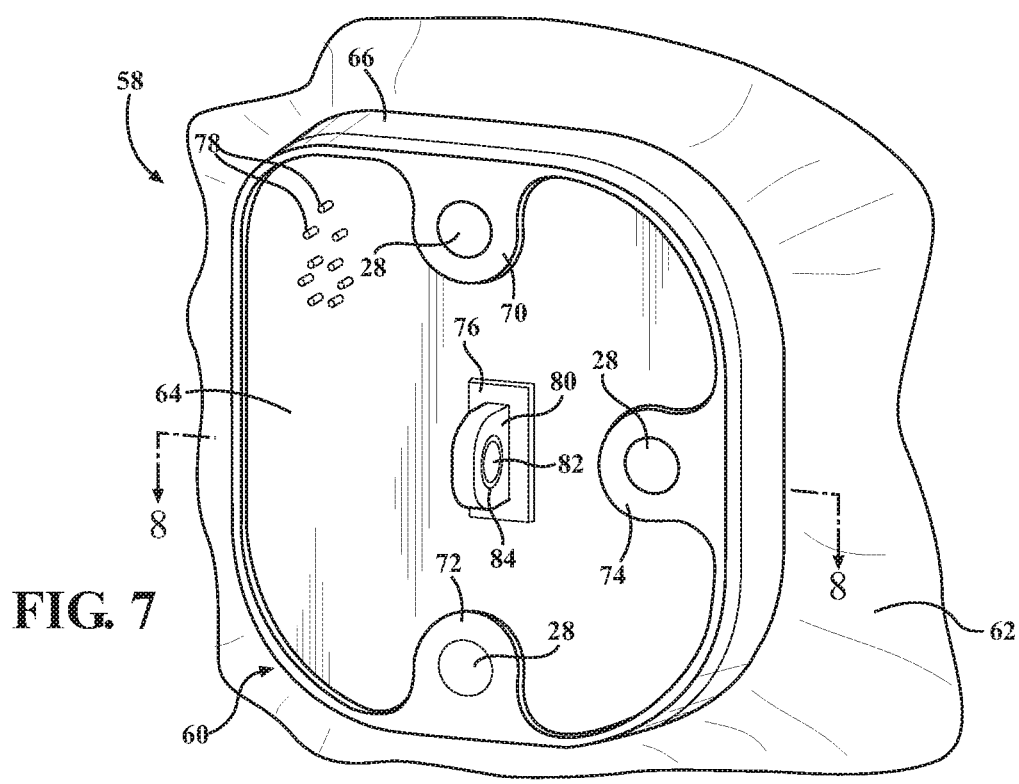

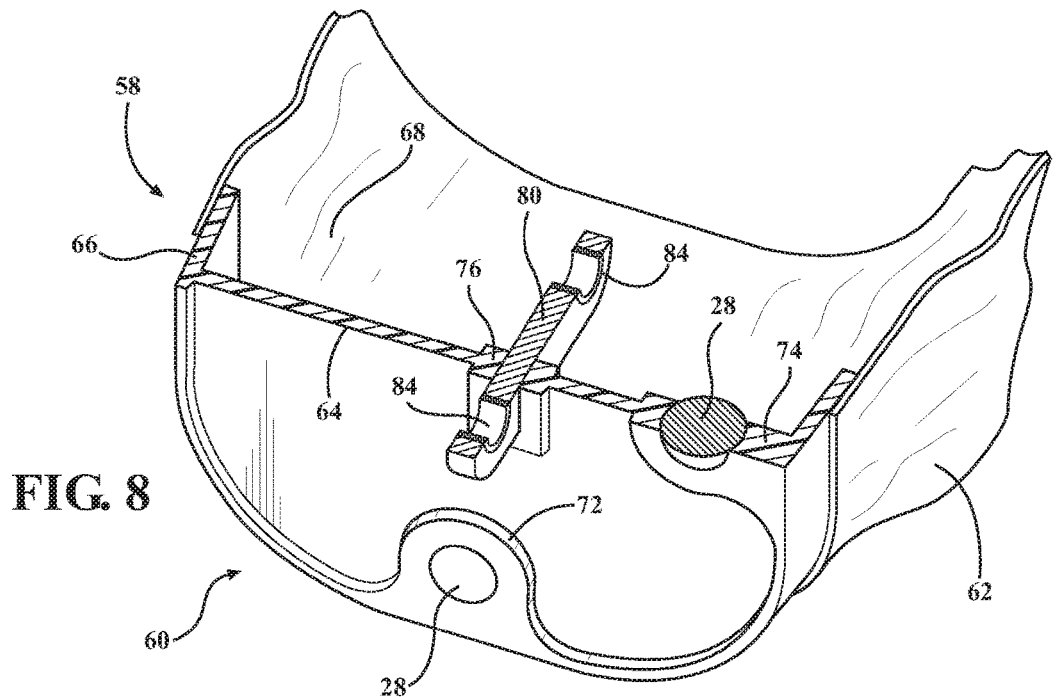
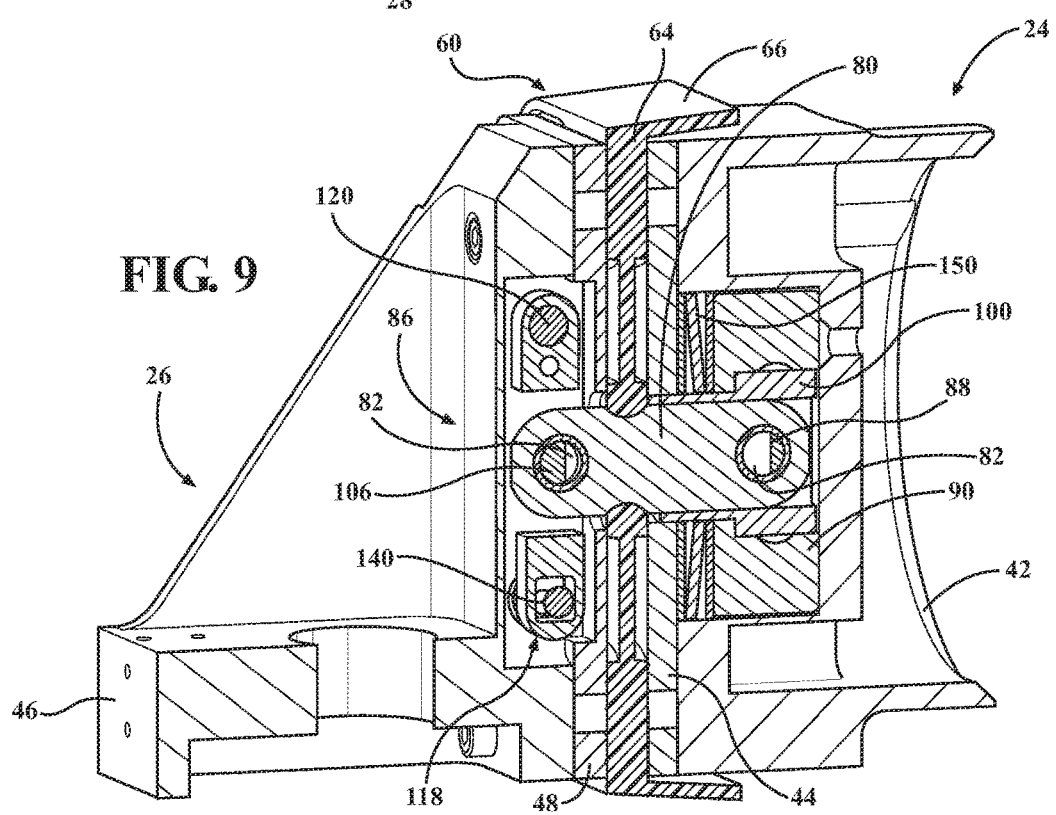

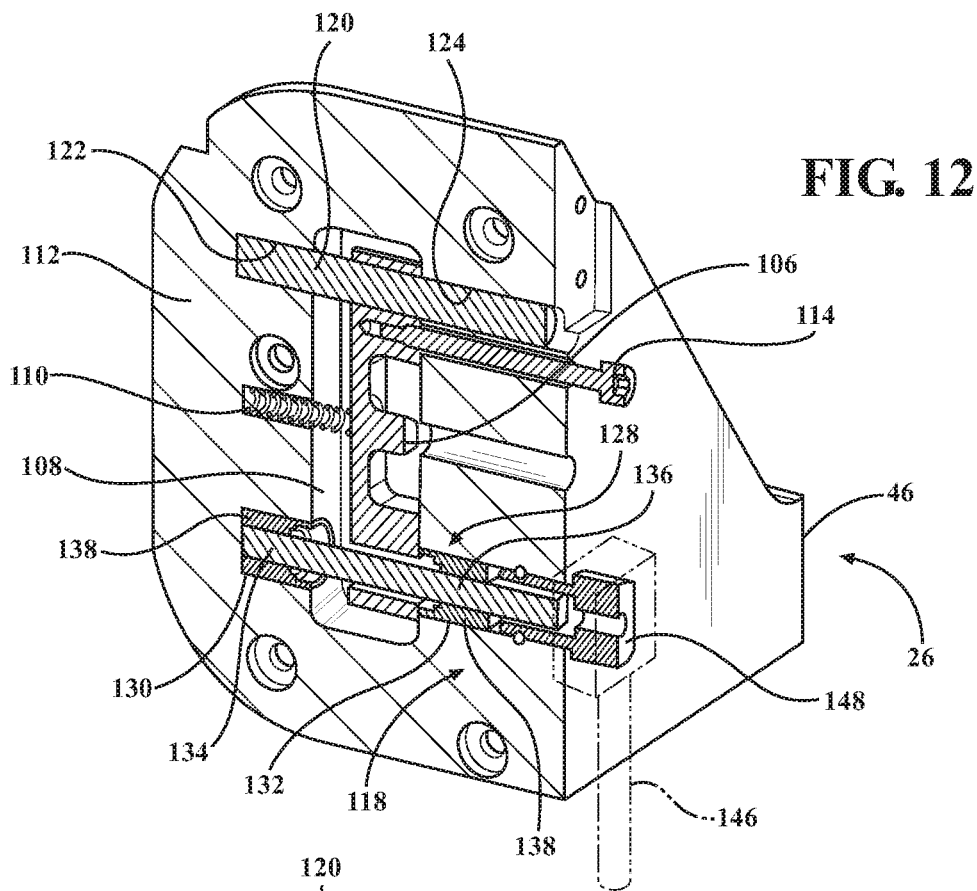
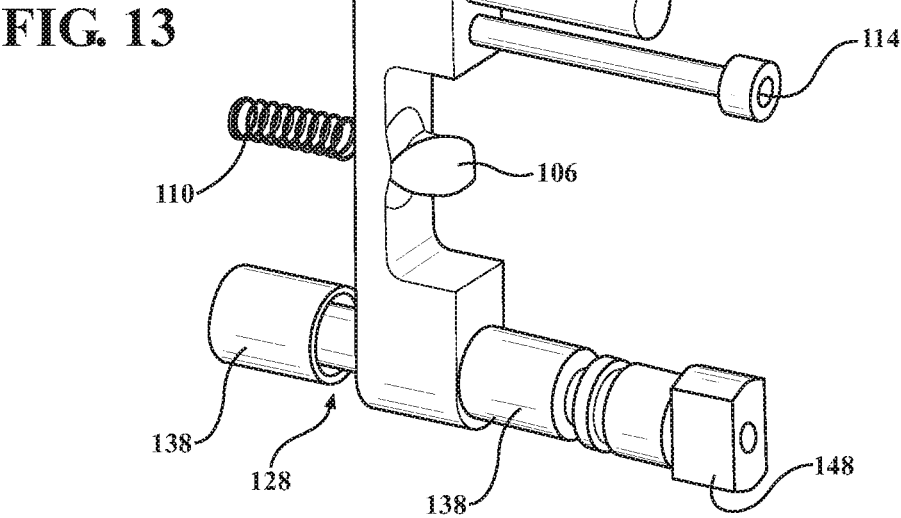

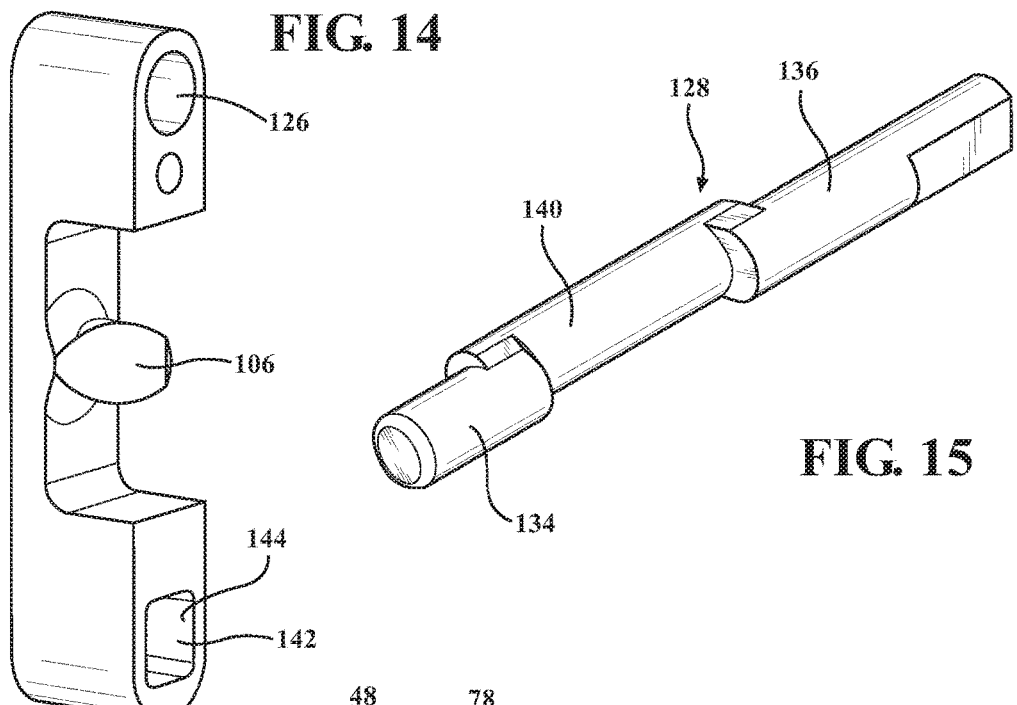
FIG. 14
FIG. 15
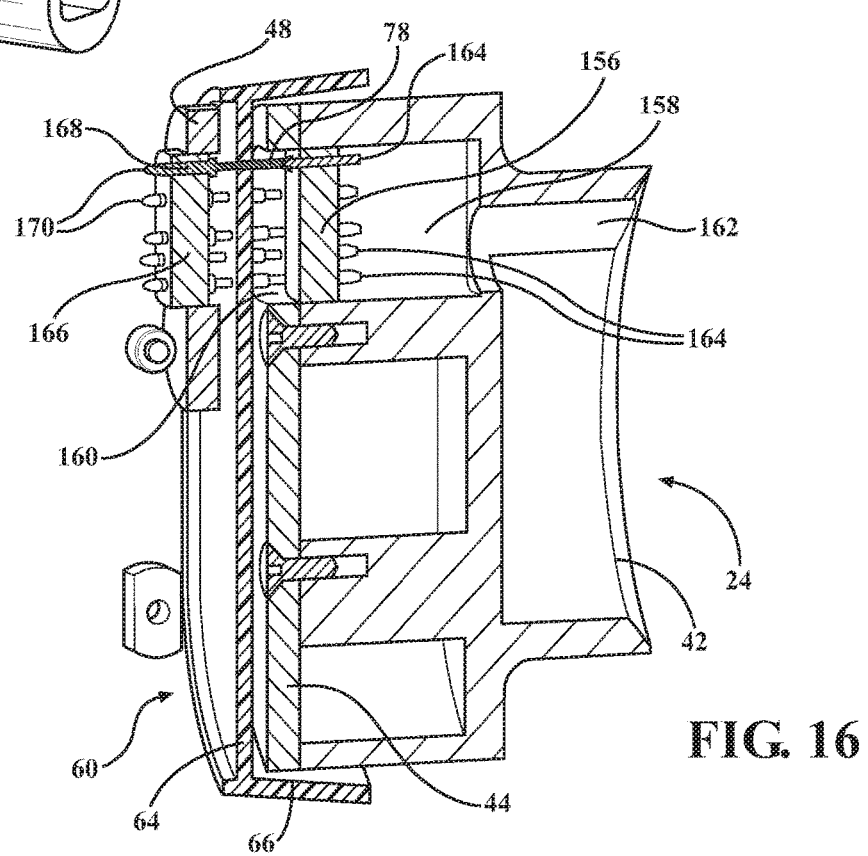
FIG. 16

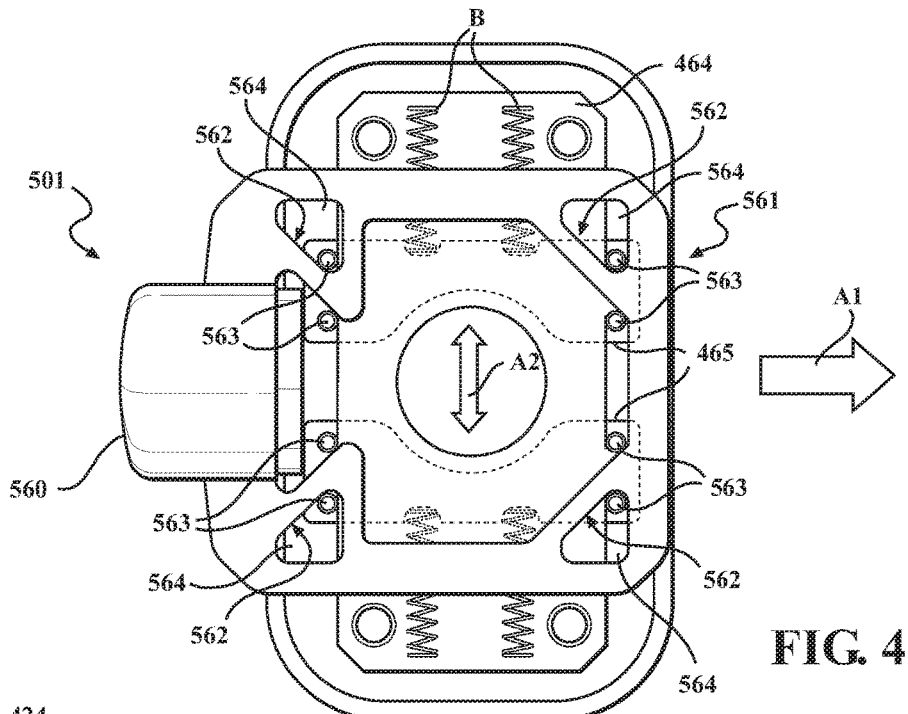
FIG. 46
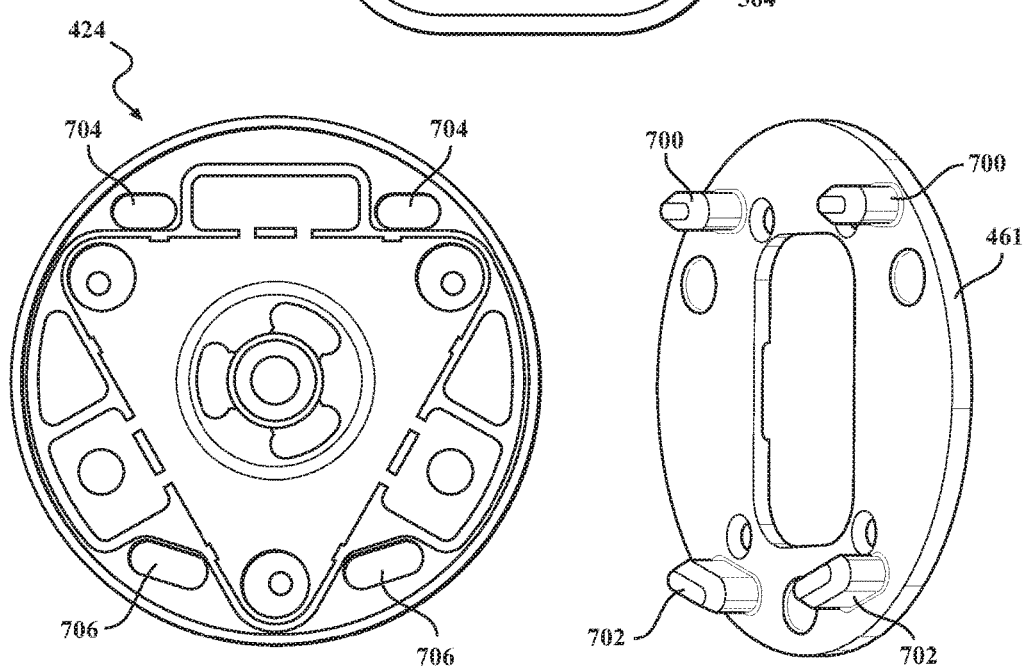
FIG. 47A
FIG. 47B

US 10,357,324 B2

STERILE BARRIER ASSEMBLY, MOUNTING SYSTEM, AND METHOD FOR COUPLING SURGICAL COMPONENTS

CROSS-REFERENCE TO RELATED APPLICATIONS

This application claims priority to and the benefit of U.S. Provisional Patent Application No. 62/118,737, filed on Feb. 20, 2015, the entire contents of which is hereby incorporated by reference herein.

TECHNICAL FIELD

The present invention relates to a sterile barrier assembly, mounting system, and method for coupling surgical components through the sterile barrier assembly.

BACKGROUND

Sterile barrier assemblies such as surgical drapes are known for establishing barriers between surgical components during surgery. For instance, a surgical drape may be used to provide a barrier between a robotic arm and an end effector attached to the robotic arm. In surgery, the robotic arm is treated as being nonsterile, while the end effector is sterile. The surgical drape creates a barrier between the robotic arm and the end effector to prevent contamination of a sterile field in which the end effector is operating.

Typically, surgical drapes placed between the robotic arm and the end effector have perforations or other openings through which different connections can be made between the robotic arm and the end effector, such as mechanical connections and/or electrical connections. Such perforations are acceptable, so long as they are covered during the surgery. If the end effector fails during the surgery and needs to be replaced, or if a different end effector is desired, and the perforations become uncovered, standard operating room sterility protocol may dictate that the surgical drape requires replacement before a different end effector can be installed. Removal of the surgical drape and installation of a new surgical drape takes up valuable time, so replacement is undesirable.

Other surgical drapes are not intentionally perforated, but instead are compressed between the robotic arm and the end effector. When compressed, if the surgical drape is formed of thin plastic, unintended rips or tears may occur. Even when the surgical drape does remain intact, positioning of the end effector on the robotic arm is imprecise as a result of the compressibility of the surgical drape. For example, the surgical drape may compress unequally. Further, a thick drape made out of conventional draping materials could deflect under normal end effector loads. Small deflections are magnified out to a tool center point (TCP) of the end effector and can become intolerable due to errors in positioning accuracy of the TCP.

Therefore, there is a need in the art for addressing one or more of these deficiencies.

SUMMARY

In one embodiment a sterile barrier assembly is provided for establishing a barrier between first and second surgical components during a surgery. The assembly includes a protective covering having a plurality of kinematic couplers. The kinematic couplers provide a kinematic coupling between the first and second surgical components through the protective covering.

In another embodiment a mounting system for coupling first and second surgical components is provided. The system includes a first mounting portion for the first surgical component and a second mounting portion for the second surgical component. The system also includes a protective covering having a plurality of kinematic couplers to kinematically couple the first and second mounting portions through the protective covering.

A method is provided in yet another embodiment for coupling first and second surgical components. The method includes placing a sterile barrier assembly having a plurality of kinematic couplers on the first surgical component. The method further includes placing the second surgical component on the sterile barrier assembly. The method further includes preloading a preload element to kinematically couple the surgical components together via the plurality of kinematic couplers through the sterile barrier assembly.

One advantage of the sterile barrier assembly, mounting system, and method is the ability to kinematically couple the first surgical component to the second surgical component through the sterile barrier assembly so that positioning is repeatable and deterministic while keeping the sterile barrier assembly intact.

BRIEF DESCRIPTION OF THE DRAWINGS

Advantages of the present invention will be readily appreciated as the same becomes better understood by reference to the following detailed description when considered in connection with the accompanying drawings wherein:

FIG. 4 is another cross-sectional perspective view of the mounting system of FIG. 2;

FIG. 5 is a front perspective view of a first mounting portion;

FIG. 6 is a front perspective view of a second mounting portion;

FIG. 7 is a front perspective view of a sterile barrier assembly;

FIG. 8 is a cross-sectional perspective view of the sterile barrier assembly;

FIG. 9 is a cross-sectional perspective view of the mounting system of FIG. 2;

FIG. 12 is a cross-sectional perspective view of the second mounting portion of FIG. 6;

FIG. 13 is a perspective view of components of a preloading mechanism;

FIG. 14 is a perspective view of a catch associated with the second mounting portion of FIG. 6;

FIG. 15 is a perspective view of a cam shaft of the preloading mechanism;

FIG. 16 is a cross-sectional perspective view illustrating electrical connections between the first and second mounting portions through the sterile barrier assembly;

FIG. 46 is an elevational view of components of an actuator used to release the alternative barrier assembly of FIG. 33 from the first mounting portion of the robot arm.

FIGS. 47A and 47B are illustrations of gross positioning features used to align the alternative barrier assembly of FIG. 33 when mounting to the first mounting portion.

DETAILED DESCRIPTION

Figure 1:
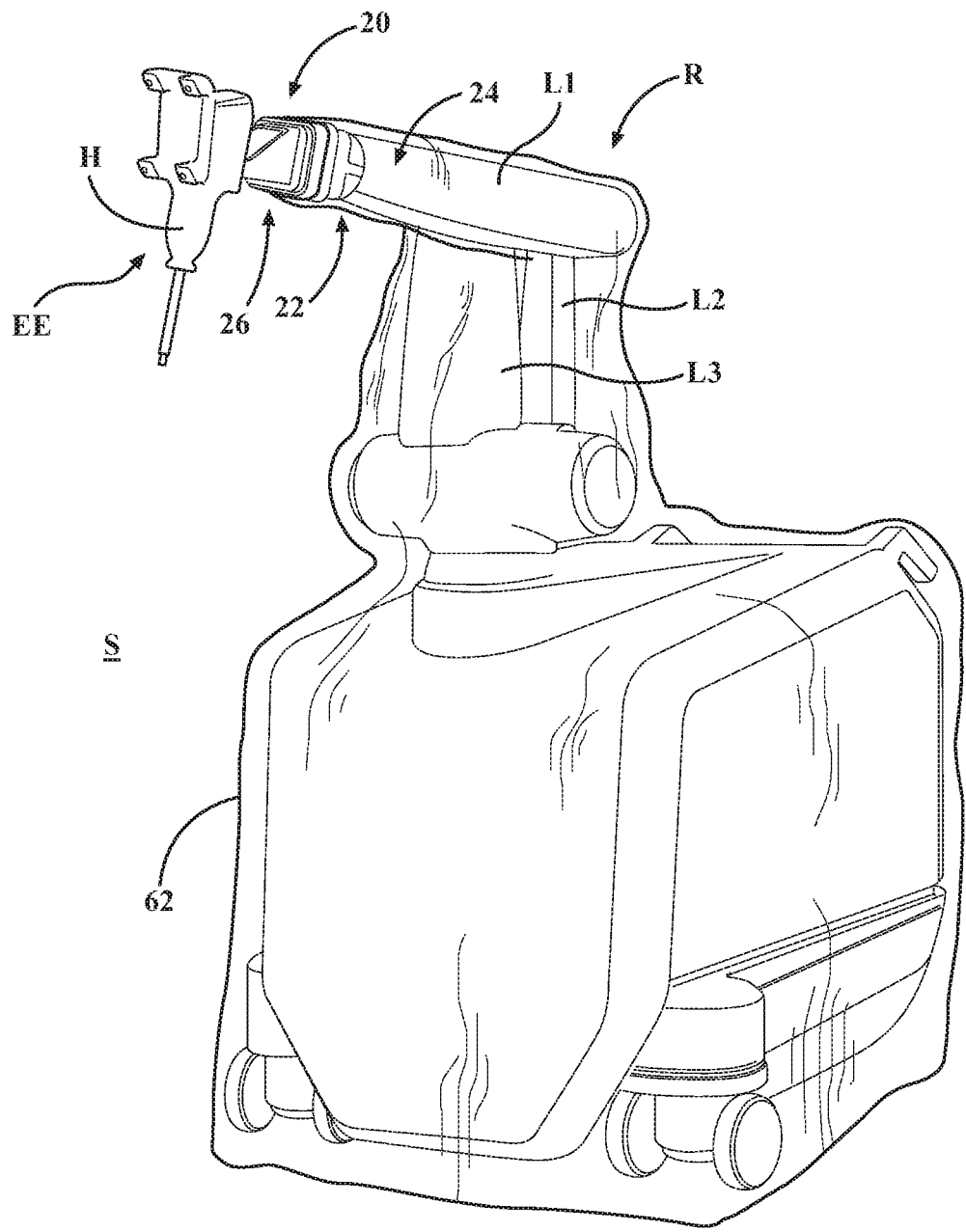
FIG. 1 is a perspective view of a robotic surgical system including a mounting system and a sterile barrier assembly.
Figure 2:
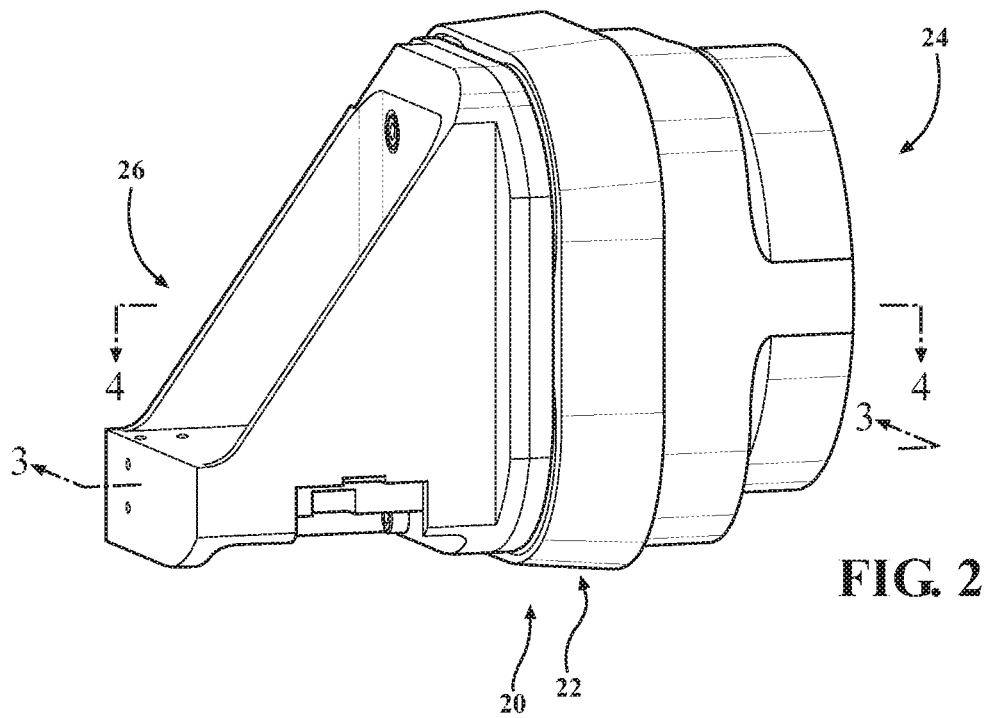
FIG. 2 is a perspective view of the mounting system.

Referring to FIGS. 1 and 2, a mounting system 20 is shown for kinematically coupling first and second surgical components using a sterile barrier assembly 22. In one embodiment described herein, the first surgical component is a robotic arm R and the second surgical component is an end effector EE for the robotic arm R. It should be appreciated that the mounting system 20 can be employed to kinematically couple any surgical components using the sterile barrier assembly 22.

The robotic arm R includes a first mounting portion 24 and the end effector EE includes a second mounting portion 26. The sterile barrier assembly 22 is located between the first and second mounting portions 24, 26 to establish a barrier between the robotic arm R and the end effector EE during surgery. This barrier separates the robotic arm R from a sterile field S in which the end effector EE is operating. During surgery, the robotic arm R is considered nonsterile and the barrier reduces the potential for migration of contaminants from the robotic arm R into the sterile field S.

The mounting portions 24, 26 are kinematically coupled together using the sterile barrier assembly 22. Kinematic coupling provides a rigid connection between the mounting portions 24, 26 so that positioning between the mounting portions 24, 26 can be deterministic and repeatable. As a result of this rigid, deterministic and repeatable connection, errors in positioning the end effector EE that may otherwise be associated with a more flexible connection can be reduced.

Kinematic coupling exactly constrains the number of degrees of freedom that are to be constrained, i.e., no degree of freedom is overconstrained. For instance, in one embodiment there are six degrees of freedom between the mounting portions 24, 26, e.g., three translational and three rotational. Thus, kinematic coupling constrains exactly those six degrees of freedom.

Figure 3:
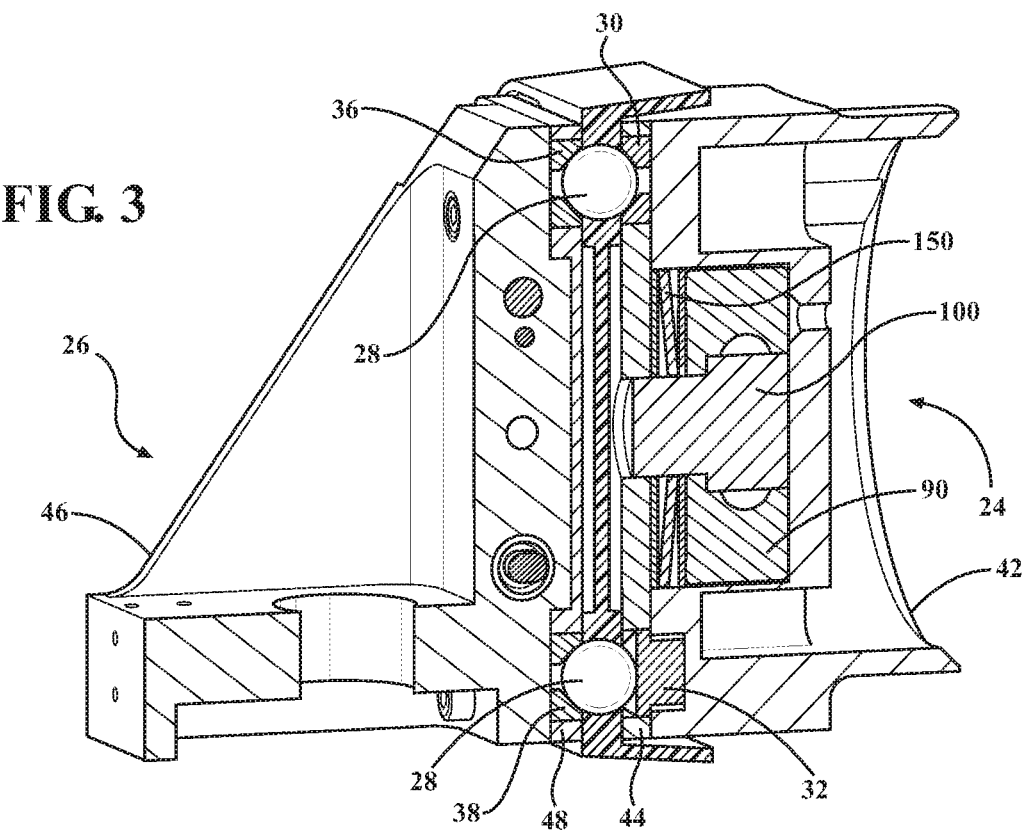
FIG. 3 is a cross-sectional perspective view of the mounting system of FIG. 2.

Referring to FIGS. 3 and 4, a plurality of kinematic couplers (also referred to as kinematic elements) of the sterile barrier assembly 22 are used to kinematically couple the mounting portions 24, 26. In the embodiment shown, the kinematic couplers are spherical balls 28. During use, the balls 28 are seated in first and second pluralities of receptacles 30, 32, 34, 36, 38, 40 of the mounting portions 24, 26. The receptacles 30, 32, 34, 36, 38, 40 are sized and shaped to receive the balls 28. In the embodiment shown, the first mounting portion 24 includes a first body 42 and a first cover plate 44 fixed to the first body 42. The first plurality of receptacles 30, 32, 34 are fixed in the first cover plate 44. The second mounting portion 26 includes a second body 46 and a second cover plate 48 fixed to the second body 46. The second plurality of receptacles 36, 38, 40 are fixed in the second cover plate 48.

Referring to FIGS. 5 and 6, the first plurality of receptacles 30, 32, 34 includes one receptacle 30 having a contact surface 50 with a conical configuration (also referred to as a cone receptacle). Another receptacle 32 has a pair of contact surfaces 52 provided by a V-shaped groove (also referred to as a V-grooved receptacle). Yet another receptacle 34 has a contact surface including a flat 54 (also referred to as a planar receptacle). The second plurality of receptacles 36, 38, 40 includes three receptacles having contact surfaces 56 with conical configurations (i.e., cone receptacles). Three balls 28 are captured between corresponding, aligned pairs of the receptacles, i.e., receptacle 30 to receptacle 36, receptacle 32 to receptacle 38, and receptacle 34 to receptacle 40, as shown in FIGS. 3 and 4. The contact surfaces 50, 52, 54, 56 of the receptacles 30, 32, 34, 36, 38, 40 act as constraint surfaces for the kinematic coupling described herein.

The receptacles 30, 32, 34, 36, 38, 40 may be formed of steel or other suitably rigid materials and may be separate components rigidly connected to the cover plates 44, 48 or may be integral with the cover plates 44, 48. The receptacles 30, 32, 34, 36, 38, 40 may be integrated into the mounting portions 24, 26, in which case the receptacles 30, 32, 34, 36, 38, 40 simply comprise constraint surfaces integral with the mounting portions 24, 26 for securing the balls 28, or the receptacles 30, 32, 34, 36, 38, 40 may otherwise be attached to the mounting portions 24, 26 in numerous ways via numerous structures.

When the mounting portions 24, 26 are brought together in approximate final orientation with the sterile barrier assembly 22 positioned therebetween, the balls 28 of the sterile barrier assembly 22 self-seat into the receptacles 30, 32, 34, 36, 38, 40. The cone receptacle, V-grooved receptacle, and planar receptacle of the first mounting portion 24 remove, three, two, and one degrees of freedom, respectively, via three, two, and one points of contact with the balls 28. Thus, exactly six degrees of freedom are constrained. In other embodiments, described further below, each of the first plurality of receptacles 30, 32, 34 of the first mounting portion 24 may remove two degrees of freedom via two points of contact with the balls 28. In either of these cases, exactly six degrees of freedom are constrained via exactly six contact points, e.g., one contact point for each degree of freedom.

Referring to FIGS. 7 and 8, the sterile barrier assembly 22 includes a protective covering 58. The protective covering 58 includes an interface 60 and a drape 62 attached to the interface 60. The drape 62 has an interior surface and an exterior surface. The interior surface is placed adjacent to the robotic arm R during surgery. In the embodiment shown the drape 62 is fitted to the robotic arm R to generally encompass the robotic arm R. The drape 62 is formed of at least one of polyethylene, polyurethane, and polycarbonate. The drape 62 may be attached to the interface 60 by ultrasonic welding, tape, adhesive, or the like. The drape 62 is attached to the interface 60 so that no perforations are present, i.e., the drape forms a continuous barrier with the interface 60.

In the embodiment shown, the interface 60 is formed of molded plastic material. The interface 60 may be formed of rubber, silicone, urethane, or other suitable materials. The interface 60 includes a main wall 64 having a perimeter and a peripheral wall 66 joining the main wall 64 at the perimeter. The peripheral wall 66 may be generally perpendicular to the main wall 64, but preferably flares slightly outwardly from perpendicular to define a cavity 68 for receiving the first mounting portion 24. The drape 62 is attached to the peripheral wall 66 of the interface 60 (See FIG. 8). The drape 62 is absent in FIGS. 2-4, 9, and 16 to better illustrate other components.

The main wall 64 has a plurality of separated support sections 70, 72, 74, 76 having a larger thickness. The main wall 64 has a width of from about 0.050 to about 0.150 inches between the support sections 70, 72, 74, 76 and a width of from about 0.150 to about 0.250 inches at the support sections 70, 72, 74, 76. The main wall 64 has a Durometer of Shore A 80.

The interface 60 includes the balls 28 integrated therein. In one embodiment, the balls 28 are insert molded in three of the support sections 70, 72, 74. As described above, the balls 28 are arranged for receipt in the first and second plurality of receptacles 30, 32, 34, 36, 38, 40 to kinematically couple the first and second mounting portions 24, 26. The balls 28 are located so that the barrier remains unbroken between the support sections 70, 72, 74 and the balls 28 to reduce the potential for migration of contaminants through the interface 60. Thus, the drape 62 and the interface 60 provide a continuous barrier to the migration of contaminants from the robotic arm R into the sterile field S.

In one embodiment, the balls 28 have polished, corrosion-resistant surfaces, so that under certain loads submicron repeatability in positioning the mounting portions 24, 26 can be achieved. The balls 28 may be formed of ceramic, stainless steel, or other suitable materials. The balls 28 may be formed of silicon carbide or tungsten carbide. The balls 28 may be precision machined to very tight tolerances, for example less than fifty millionths of an inch.

The interface 60 includes a plurality of electrical terminals. In the embodiment shown, the electrical terminals are pins 78 that may be insert molded into the main wall 64. The pins 78 are located so that the barrier remains unbroken between the main wall 64 and the pins 78 to reduce the potential for contaminants to migrate through the interface 60. The pins 78 transfer electrical power/signals across the sterile barrier assembly 22.

The interface 60 includes a preloading element. In the embodiment shown, the preloading element is an elongated load bar 80. The load bar 80 may be insert molded into one of the support sections. The load bar 80 is formed with rounded indentations on sides thereof to facilitate embedding in the support section so that the load bar 80 remains fixed to the interface 60 during use. The load bar 80 is located such that the barrier remains unbroken between the support section and the load bar 80 to reduce the potential for migration of contaminants through the interface 60. Thus, the drape 62 and interface 60 provide a continuous barrier to the migration of contaminants from the robotic arm R into the sterile field S.

The load bar 80 has first and second ends. The load bar 80 may be formed of stainless steel, Kevlar composite, or other suitably rigid materials. The load bar 80 defines apertures 82 near each of the ends. Inserts 84 are located in the apertures 82. The inserts 84 are in the form of cylindrical bushings. The inserts 84 are formed of stainless steel or silicone nitride. In some embodiments, the load bar 80 is employed without inserts.

Figure 10:
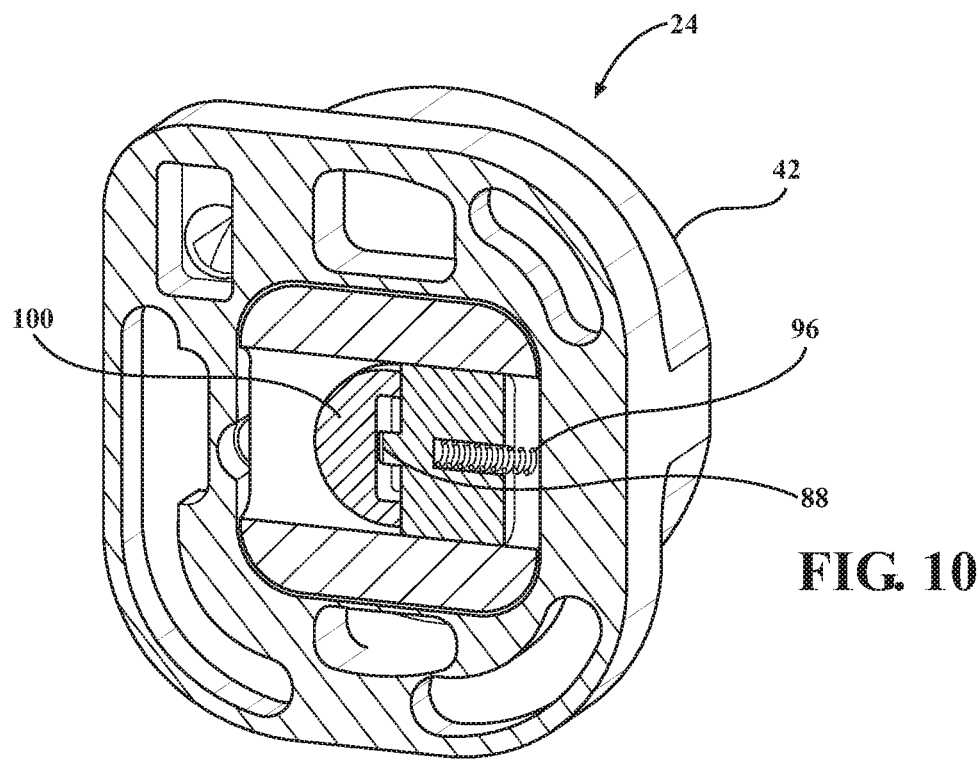
FIG. 10 is a cross-sectional perspective view of the first mounting portion of FIG. 5.
Figure 11:
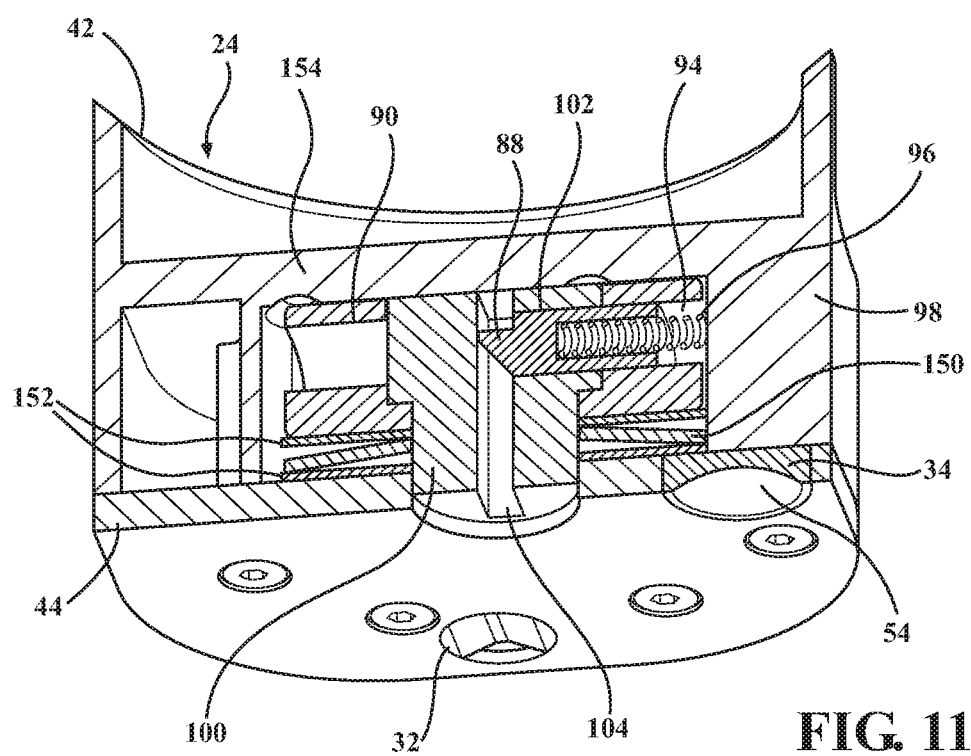
FIG. 11 is a cross-sectional perspective view of the first mounting portion of FIG. 5.
Figure 17:
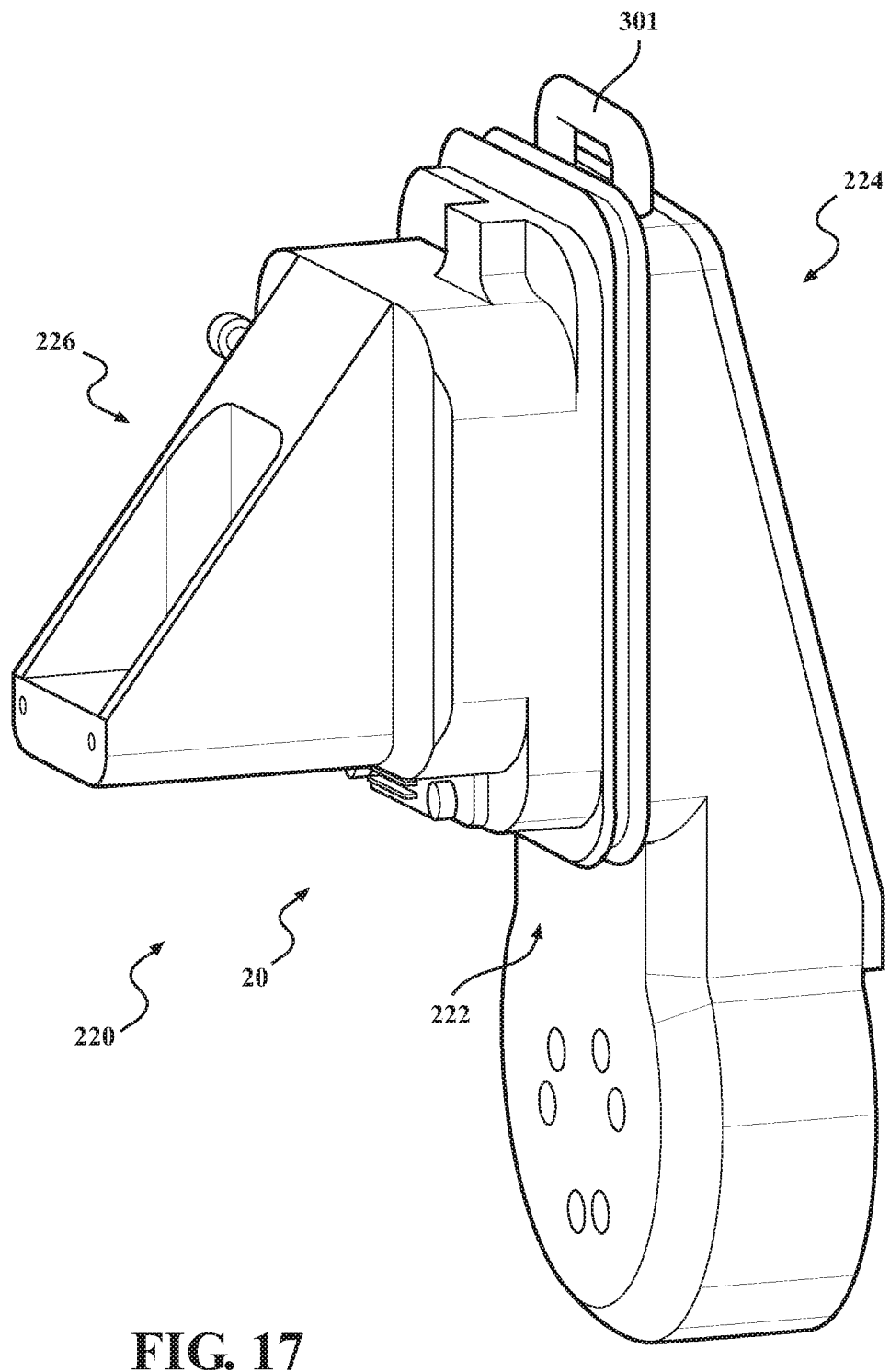
FIG. 17 is a perspective view of an alternative mounting system.

Referring to FIGS. 9-11, a preloading mechanism 86 clamps the mounting portions 24, 26 in position once they are brought together in approximate final orientation. In the embodiment shown, the load bar 80 forms part of the preloading mechanism 86 and also acts as an initial support member to hold the protective covering 58 on the robotic arm R. A preload force is applied to the load bar 80. The preload force is sized to exceed anticipated loading through the kinematic coupling so that the kinematic coupling and associated properties are maintained.

The preloading mechanism 86 further includes a first catch 88. The first catch 88 is slidably disposed in a catch guide 90 to move from an unlatched position to a latched position. The catch guide 90 is held in a first inner cavity 92 (see FIG. 4) defined in the first body 42. The catch guide 90 defines an oblong through passage 94 in which the first catch 88 slides.

As shown in FIG. 11, a first spring 96 biases the first catch 88 laterally from a side wall 98 of the first body 42 into the latched position. A first release button (not shown) can be slidably disposed in the first body 42 to release the first catch 88. The first release button may simply be depressed to slide the first catch 88 from the latched position to the unlatched position.

A load bar receiver 100 defines another oblong passage 102. The oblong passages 94, 102 of the catch guide 90 and the receiver 100 align with one another so that the first catch 88 is slidable therein to move from the unlatched position to the latched position. The receiver 100 is cylindrical. The receiver 100 further defines a load bar slot 104 therethrough. The load bar slot 104 is arranged perpendicularly to the oblong passage 102 in the receiver 100 to receive the first end of the load bar 80.

During use, the first end of the load bar 80 is inserted into the load bar slot 104 until one of the apertures 82 in the load bar 80 is engaged by the first catch 88 (see FIGS. 4 and 9). Once the load bar 80 is fully engaged by the first catch 88, the sterile barrier assembly 22 is generally supported on the first mounting portion 24 for further manipulation. Thus, the load bar 80 and the first catch 88 function as an initial support mechanism for the sterile barrier assembly 22.

Referring to FIGS. 9 and 12-15, the preloading mechanism 86 further includes a second catch 106. The second catch 106 is slidably disposed in the second body 46. More specifically, the second mounting portion 26 defines a second inner cavity 108 in which the second catch 106 is slidable between unlatched and latched positions.

A second spring 110 biases the second catch 106 laterally from a side wall 112 of the second body 46 into the latched position. A second release button 114, like the first, can be slidably disposed in the second body 46 to release the second catch 106. The second release button 114 may simply be depressed to slide the second catch 106 from the latched position to the unlatched position.

The second cover plate 48 fixed to the second body 46 has an elongated slot 116 (see FIG. 6) sized to receive the second end of the load bar 80 opposite the first end inserted into the receiver 100.

During use, the second end of the load bar 80 is inserted into the elongated slot 116 until the other aperture 82 in the load bar 80 is engaged by the second catch 106. Once the load bar 80 is fully engaged by the second catch 106, the sterile barrier assembly 22 and the second mounting portion 26 are generally supported on the first mounting portion 24 for further installation. Thus, the load bar 80, the first catch 88, and the second catch 106 also function as a support mechanism for the sterile barrier assembly 22 and the second mounting portion 26.

As shown in FIG. 9, the preloading mechanism further includes a tensioner 118 operatively coupled to the load bar 80. The tensioner 118 applies tension to the load bar 80 and clamps the first and second mounting portions 24, 26 together with the preload force such that the balls 28 seat into the first and second plurality of receptacles 30, 32, 34, 36, 38, 40.

Referring to FIGS. 12 and 13, the tensioner 118 applies tension to the load bar 80 by moving the second catch 106 with respect to the first catch 88. The second catch 106, while slidable in the second body 46 between unlatched and latched positions, is also pivotally supported in the second body 46 about a pivot shaft 120. The pivot shaft 120 is located in a pair of support bores 122, 124 in the second body 46. The second catch 106 defines a pivot bore 126 (see FIG. 14) therethrough for receiving the pivot shaft 120. As a result, the second catch 106 is able to pivot about the pivot shaft 120.

The tensioner 118 includes a cam shaft 128. The cam shaft 128 is rotatable between tensioned and untensioned positions. The cam shaft 128 is rotatably supported in a pair of support bores 130, 132 in the second body 46. The cam shaft 128 has first and second cylindrical shaft sections 134, 136 that are rotatably supported in the support bores 130, 132 by bushings 138.

The cam shaft 128 includes a cam section 140 (see FIGS. 9 and 15) between the first and second shaft sections 134, 136. The cam section 140 is offset from the first and second shaft sections 134, 136. The cam section 140 is disposed in a cam passage 142 defined in the second catch 106 (see FIG. 14). The cam passage 142 is rectangular in shape and extends through the second catch 106 near one end of the second catch 106, while the pivot bore 126 extends through the second catch 106 near an opposite end. When the cam shaft 128 begins rotation toward the tensioned position, the cam section 140 contacts an inner surface 144 defining the cam passage 142. Further rotation of the cam shaft 128 causes additional camming action by the cam section 140 against the inner surface 144 which pivots the second catch 106 about the pivot shaft 120 so that tension is placed on the load bar 80.

The tensioner 118 also includes a lever 146 rotatably fixed to the cam shaft 128 via a lever attachment 148. The lever attachment 148 has a geometric shape that conforms to a shape of a cavity (not shown) in the lever 146 so that actuation of the lever 146 results in rotation of the cam shaft 128. The cam shaft 128 is rotated at least ninety degrees to move between the untensioned and tensioned positions. Of course, other positions therebetween may place tension on the load bar 80 and could be suitable for applying the desired preload force.

The lever 146 is locked when the cam shaft 128 is placed in the desired position, e.g., the tensioned position. In the tensioned position, the preload tensile force is applied to the load bar 80. By locking the lever 146 after applying the preload force, the preload force is continually applied during use of the robotic arm R and end effector EE to maintain the kinematic coupling. The preloading mechanism 86 transfers the preload force across the sterile barrier assembly 22 without piercing the barrier.

When the tensioner 118 applies the preload force to the load bar 80, a disc spring 150 applies a compressive force equal to the preload force to the load bar 80. The disc spring 150 is contained between two spring shims 152. The disc spring 150 biases the catch guide 90, receiver 100, and first catch 88 toward a rear wall 154 of the first body 42. The disc spring 150 biases the load bar 80 by virtue of the load bar 80 being latched to the first catch 88.

As the balls 28 are aligned within the first and second plurality of receptacles 30, 32, 34, 36, 38, 40, and the preload force is applied, some stretching and/or flexing of the interface 60 is possible between the balls 28 so that the balls 28 properly seat in the receptacles 30, 32, 34, 36, 38, 40, particularly when the second plurality of receptacles 36, 38, 40 have conical configurations (which engage each of the balls 28 at three contact points). This stretching and/or flexing occurs without breaking the barrier. Thus, the balls 28 are able to move into the receptacles 30, 32, 34, 36, 38, 40 upon preloading. These properties of the interface 60 account for manufacturing tolerances. In other words, the interface 60 is able to stretch and/or flex without breaking contact or a seal with the balls 28, such as the contact or seal created during molding.

Once seated, positions of the balls 28 are fixed relative to the first and second plurality of receptacles 30, 32, 34, 36, 38, 40. As a result, the first and second mounting portions 24, 26 are kinematically coupled together without piercing the sterile barrier assembly 22. The kinematic coupling allows the end effector EE to be readily released from and rejoined to the robotic arm R at the same location. The kinematic coupling also allows the end effector EE to be readily released from the robotic arm R so that different end effectors with similar mounting portions can be kinematically coupled to the robotic arm R.

FIG. 16 shows electrical power and/or other signal connections that can be made through the sterile barrier assembly 22. These connections employ the pins 78. These pins 78 electrically interconnect electrical connectors attached to the first and second mounting portions 24, 26.

In the embodiment shown in FIGS. 5, 6, and 16, the first mounting portion 24 includes a first electrical connector base 156. The first electrical connector base 156 is fixed in a communication cavity 158 defined in the first body 42. The first cover plate 44 defines an opening 160 into the communication cavity 158. A wireway 162 is also defined in the first body 42 to carry wires away from the first electrical connector base 156. A plurality of pogo pin connectors 164, e.g., spring-loaded electrical connectors, are movably supported by the first electrical connector base 156.

The second mounting portion 26 includes a second electrical connector base 166. The second electrical connector base 166 is fixed in an opening 168 in the second cover plate 48. A plurality of electrical receiver terminals 170 are supported by the second electrical connector base 166. When the first and second mounting portions 24, 26 are kinematically coupled together and preloaded, the electrical receiver terminals 170 receive the pins 78 of the interface 60. Likewise, the pogo pin connectors 164 make contact with the pins 78 of the interface 60 so that power or other electrical signals can flow through the pins 78. Thus, power, communication signals, or other signals can be passed from the robotic arm R to the end effector EE and vice versa.

Referring to FIGS. 17-32, an alternative mounting system 220 is shown for kinematically coupling the first and second surgical components (e.g., robotic arm R and end effector EE) using a sterile barrier assembly 222.

In this embodiment, the robotic arm R includes a first mounting portion 224 and the end effector EE includes a second mounting portion 226. The sterile barrier assembly 222 is located between the first and second mounting portions 224, 226 to establish the barrier between the robotic arm R and the end effector EE during surgery.

Figure 18:
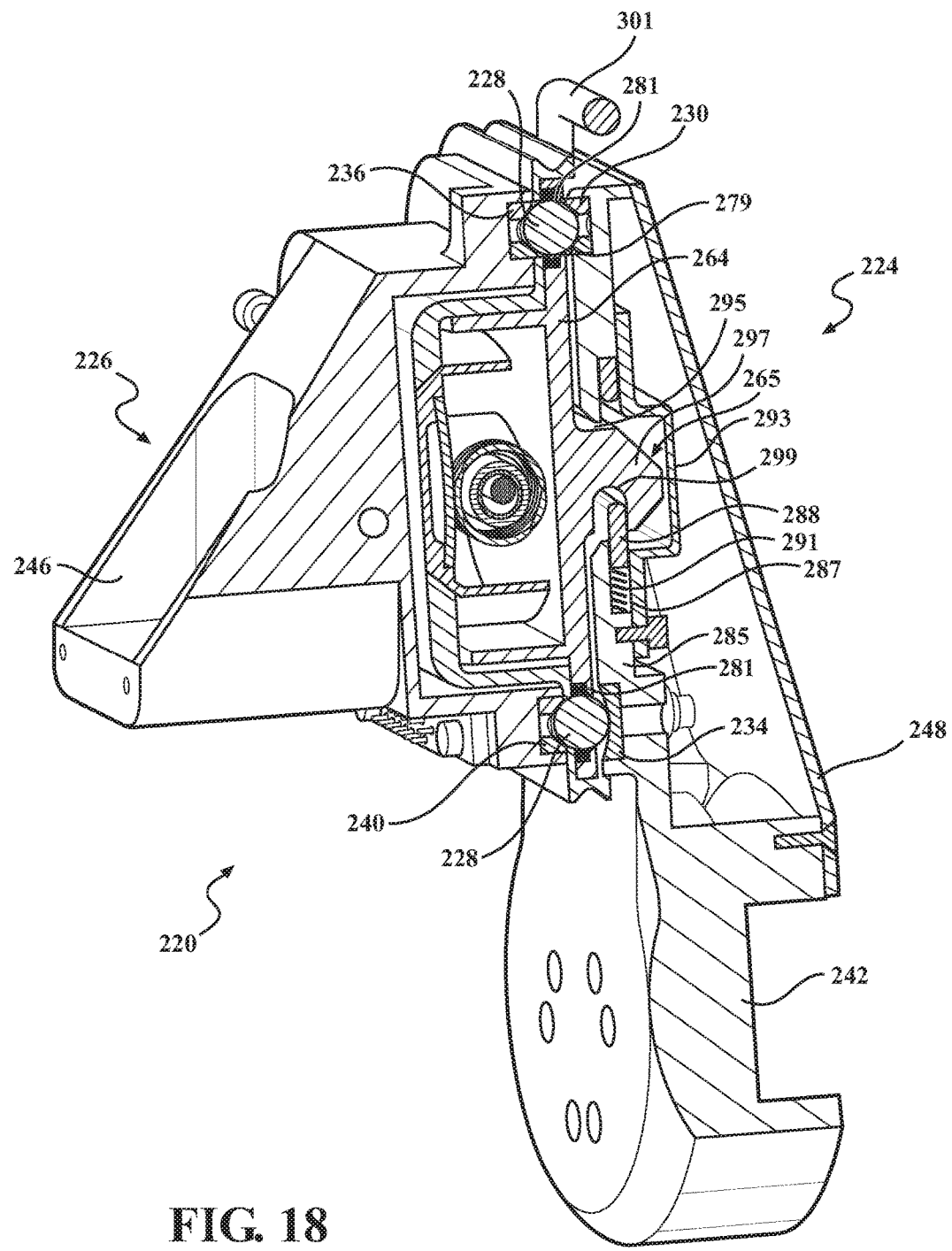
FIG. 18 is a cross-sectional perspective view of the alternative mounting system of FIG. 17.
Figure 19:
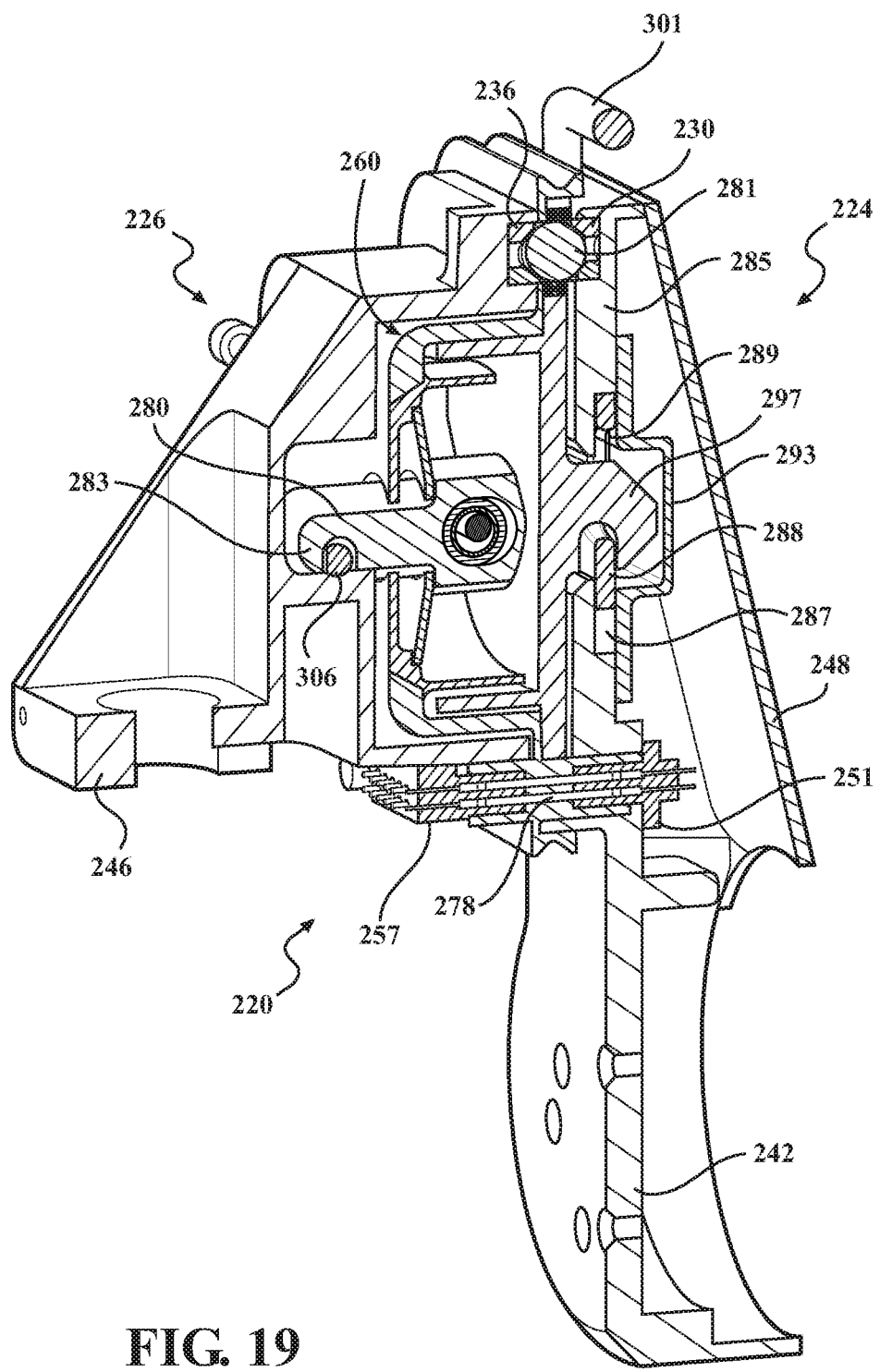
FIG. 19 is another cross-sectional perspective view of the alternative mounting system of FIG. 17.

Referring to FIGS. 18 and 19, a plurality of kinematic couplers are used to kinematically couple the first and second mounting portions 224, 226. In this embodiment, the kinematic couplers are spherical balls 228. The balls 228 are seated in first and second pluralities of receptacles 230, 232, 234, 236, 238, 240. The receptacles 230, 232, 234, 236, 238, 240 are sized and shaped to receive the balls 228. The first mounting portion 224 includes a first body 242 and a first cover plate 248 fixed to the first body 242. The first plurality of receptacles 230, 232, 234 are fixed in the first body 242. The second mounting portion 226 includes a second body 246. The second plurality of receptacles 236, 238, 240 are fixed in the second body 246.

Figure 20:
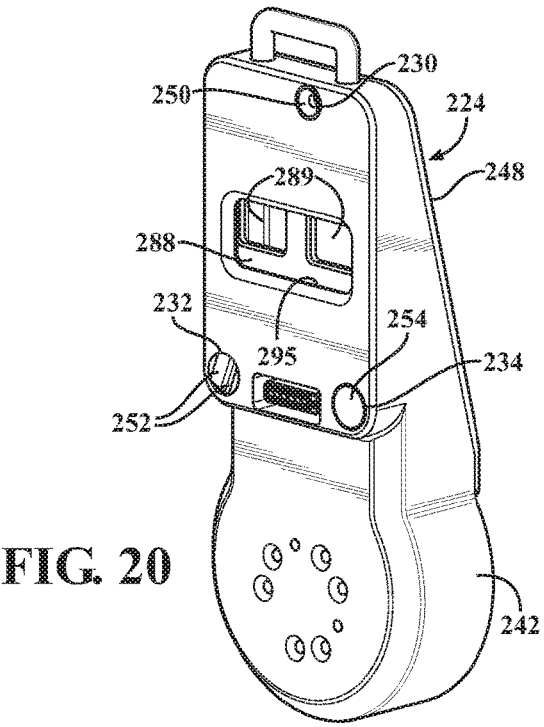
FIG. 20 is a front perspective view of a first mounting portion.

Referring to FIG. 20, the first plurality of receptacles 230, 232, 234 includes one receptacle 230 having a contact surface 250 with a conical configuration (also referred to as a cone receptacle). Another receptacle 232 has a pair of contact surfaces 252 provided by a V-shaped groove (also referred to as a V-grooved receptacle). Yet another receptacle 234 has a contact surface 254 including a flat (also referred to as a planar receptacle). The contact surfaces 252 of the V-grooved receptacle or the contact surface 254 of the planar receptacle may be generally flat or may be concave with the surfaces 252, 254 having a concavity that results in only a single point of contact with the balls 228. In some versions, the contact surfaces 252 of the V-grooved receptacle are in the shape of a gothic arch.

Figure 21:
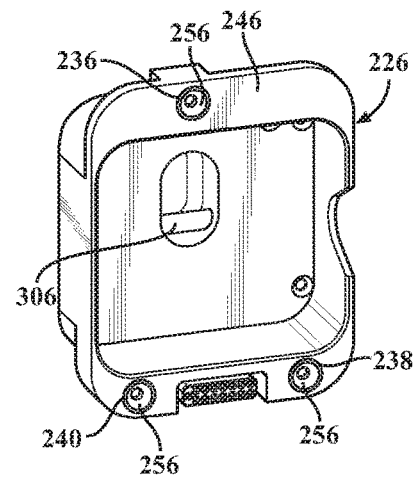
FIG. 21 is a front perspective view of a second mounting portion.
Figure 22:
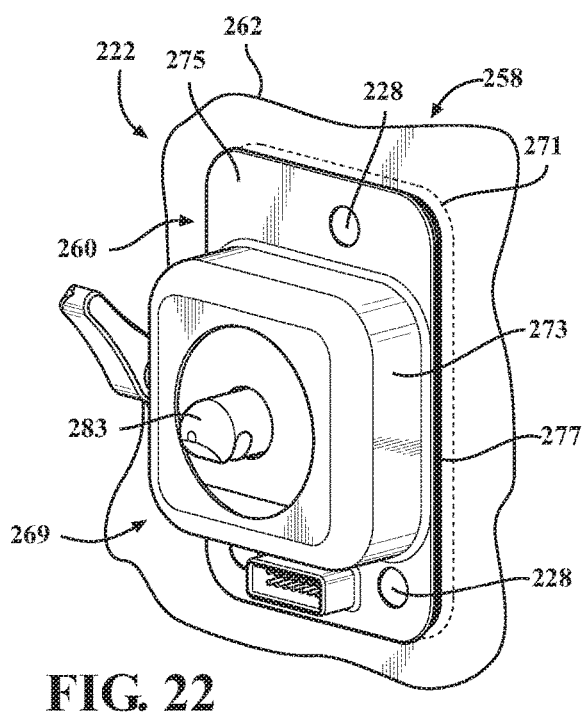
FIG. 22 is a front perspective view of an alternative sterile barrier assembly.
Figure 23:
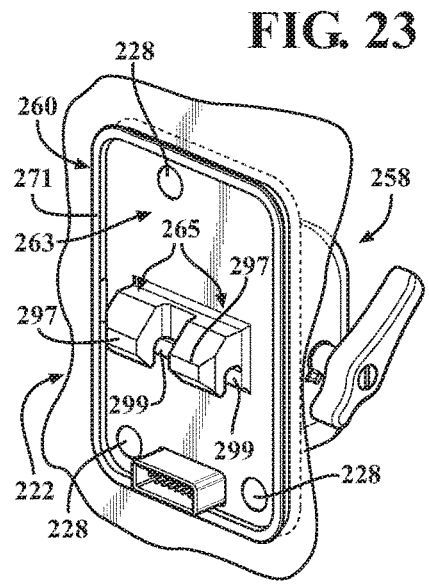
FIG. 23 is a rear perspective view of the alternative sterile barrier assembly.

The second plurality of receptacles 236, 238, 240 includes three receptacles having contact surfaces 256 with conical configurations (i.e., cone receptacles). Three balls 228 are captured between corresponding, aligned pairs of the receptacles, i.e, receptacle 230 to receptacle 236, receptacle 232 to receptacle 238, and receptacle 234 to receptacle 240, as shown in FIGS. 20 and 21.

The receptacles 230, 232, 234, 236, 238, 240 may be formed of steel or other suitably rigid materials and may be separate components rigidly connected to the bodies 242, 246 or may be integral with the bodies 242, 246. The receptacles 230, 232, 234, 236, 238, 240 may be integrated into the mounting portions 224, 226 or otherwise attached to the mounting portions 224, 226 in numerous ways.

When the mounting portions 224, 226 are brought together in approximate final orientation with the sterile barrier assembly 222 positioned therebetween, the balls 228 of the sterile barrier assembly 222 self-seat into the receptacles 230, 232, 234, 236, 238, 240. The cone receptacle, V-grooved receptacle, and planar receptacle of the first mounting portion 224 remove, three, two, and one degrees of freedom, respectively. Thus, exactly six degrees of freedom are constrained. In other embodiments, described further below, each of the first plurality of receptacles 230, 232, 234 of the first mounting portion 224 may remove two degrees of freedom via two points of contact with the balls 228. In either of these cases, exactly six degrees of freedom are constrained via exactly six contact points, e.g., one contact point for each degree of freedom.

Referring to FIGS. 22-26, the sterile barrier assembly 222 includes a protective covering 258. The protective covering 258 includes an interface 260 and a drape 262 attached to the interface 260. The drape 262 has an interior surface and an exterior surface. The interior surface is placed adjacent to the robotic arm R during surgery. In this embodiment, the drape 262 is fitted to the robotic arm R to generally encompass the robotic arm R. The drape 262 is formed of at least one of polyethylene, polyurethane, and polycarbonate. The drape 262 may be attached to the interface 260 by ultrasonic welding, tape, adhesive, or the like. The drape 262 is attached to the interface 260 so that no perforations are present or are sealed, i.e., the drape forms a continuous barrier with the interface 260. The drape 62 is absent in FIGS. 17-19 and 24-27 to better illustrate other components.

Figure 25:
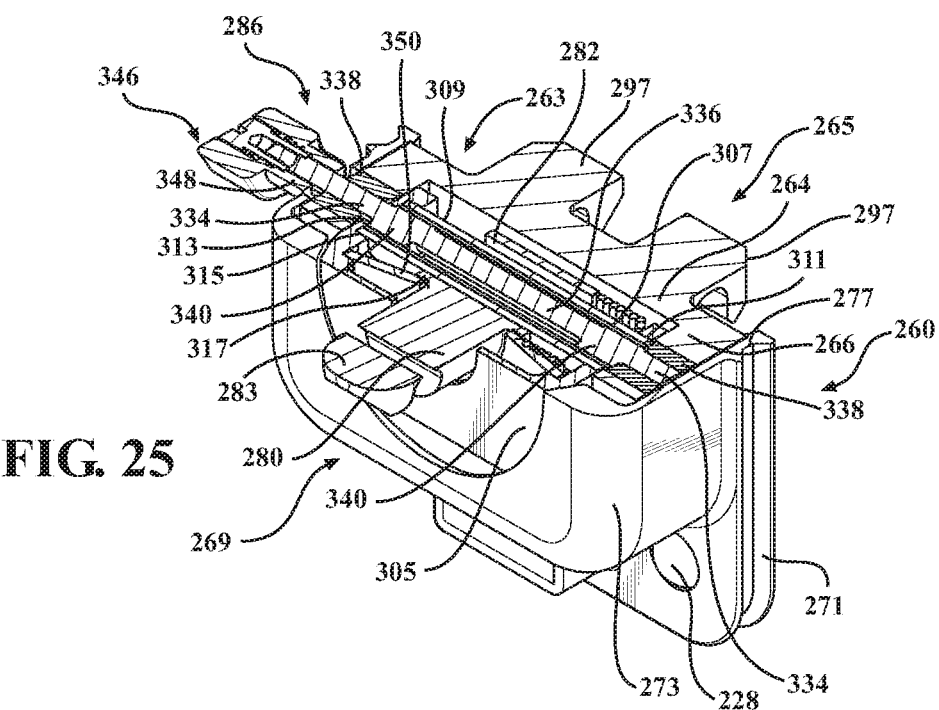
FIG. 25 is a cross-sectional perspective view of the alternative sterile barrier assembly (without drape)
Figure 26:
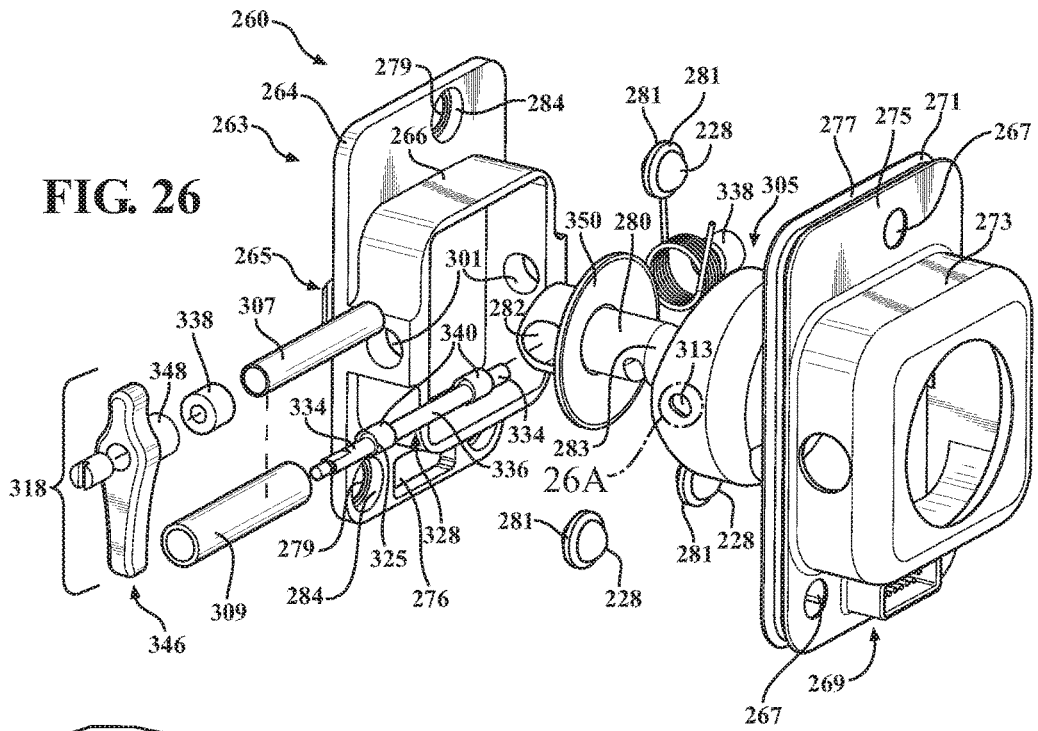
FIG. 26 is an exploded perspective view of the alternative sterile barrier assembly (without drape)

Referring to FIGS. 25 and 26, in the embodiment shown, the interface 260 includes a latch bracket 263 formed of a rigid material such as aluminum or stainless steel. The latch bracket 263 includes a main wall 264 (see FIG. 26) having a perimeter and an inner wall 266 extending from the main wall 264. The inner wall 266 may be generally perpendicular to the main wall 264. The latch bracket 263 includes a pair of latches 265 (see also FIG. 23) extending from the main wall 264 in a direction opposite the inner wall 266. The latches 265 may be in the form of latch hooks. The latches 265 interact with and engage a first catch 288 of the first mounting portion 224 as described below.

The interface 260 further includes a cover 269 having a peripheral lip 271. The cover 269 may be formed of injection molded plastic. The peripheral lip 271 snap-fits over the main wall 264 so that the cover 269 is secured to the latch bracket 263. When secured, the cover 269 includes an outer wall 273 surrounding the inner wall 266 of the latch bracket 263. The cover 269 also includes a wall 275. The wall 275 extends from a base of the outer wall 273 to the peripheral lip 271. In addition to the snap-fit connection, the cover 269 may be fixed to the latch bracket 263 by adhesive between the wall 275 and the main wall 264 of the latch bracket 263.

A seal (not shown) may be located between an edge of the main wall 264 and an inner edge of the peripheral lip 271 to further enhance the barrier.

The peripheral lip 271 defines an attachment groove 277 in which the drape 262 is attached to the interface 260. The attachment groove 277 may receive, for example, an elastic band of the drape 262, tape for the drape 262, a snap-ring of the drape 262, and the like.

The interface 260 includes the balls 228 integrated therein. In this embodiment, the balls 228 are located in ball openings defined in the main wall 264 of the latch bracket 263. The ball openings are sized so that a portion of each of the balls 228 protrudes on either side of the main wall 264. The main wall 264 includes a stop 279 in each of the ball openings. In the embodiment shown, the stop 279 is a radially inwardly directed tapered surface of the main wall 264. The tapered surface defines an opening having a diameter slightly smaller than a diameter of the balls 228 to prevent the balls 228 from passing entirely through the main wall 264 (see FIG. 18).

During assembly the balls 228 are dropped into the ball openings in the main wall 264. The stop 279 prevents the balls 228 from passing entirely through the ball openings while still allowing a portion of the balls 228 to protrude beyond the main wall 264. The cover 269 is then snap-fit over the latch bracket 263 to hold the balls 228 in place in the ball openings. The wall 275 of the cover 269 defines a plurality of secondary ball openings 267 that are in line with the ball openings in the main wall 264 yet sized slightly smaller than a diameter of the balls 228. As a result, the balls 228 are able to protrude beyond the wall 275 yet be held in placed between the wall 275 and the main wall 264.

The main wall 264 has a plurality of counterbores 284 that further define the ball openings. The counterbores 284 are sized with a diameter slightly larger than each of the balls 228 so that the balls 228 can be seated in the ball openings. The counterbores 284 are also sized so that seals 281 such as o-rings can be placed in the counterbores 284 to seal about the balls 228 and against the main wall 264. As shown, two seals 281 are located in each of the counterbores 284 (see also FIG. 18). The seals 281 are held in place by virtue of the wall 275 being located over the seals 281. The wall 275 engages one of each pair of seals 281 to further enhance the barrier.

The seals 281 are resilient so that the balls 228 are able to move slightly laterally in the ball openings, e.g., the balls 228 are not constrained from lateral movement in the ball openings. As a result, distances between the balls 228 are able to adjust, e.g., increase or decrease, so that the balls 228 seat properly into the receptacles 230, 232, 234, 236, 238, 240, particularly when each of the second plurality of receptacles 236, 238, 240 have conical configurations, which are rigidly fixed in position relative to one another. Owing to the ability of the balls 228 to adjust laterally, the balls 228 are able to fit neatly into the conical receptacles, thereby enabling three points of contact with the balls 228.

As described above, the balls 228 are arranged for receipt in the first and second plurality of receptacles 230, 232, 234, 236, 238, 240 to kinematically couple the first and second mounting portions 224, 226. The balls 228 are located so that the barrier remains unbroken between the main wall 264 and the balls 228 to reduce the potential for migration of contaminants through the interface 260. Thus, the drape 262 and interface 260 provide a continuous barrier to the migration of contaminants from the robotic arm R into the sterile field S.

In this embodiment, the balls 228 have polished, corrosion-resistant surfaces, so that under certain loads submicron repeatability in positioning the mounting portions 224, 226 can be achieved. The balls 228 may be formed of ceramic, stainless steel, or other suitable materials. The balls 228 may be formed of silicon carbide or tungsten carbide. The balls 228 may be precision machined to very tight tolerances, for example less than fifty millionths of an inch.

Figure 24:
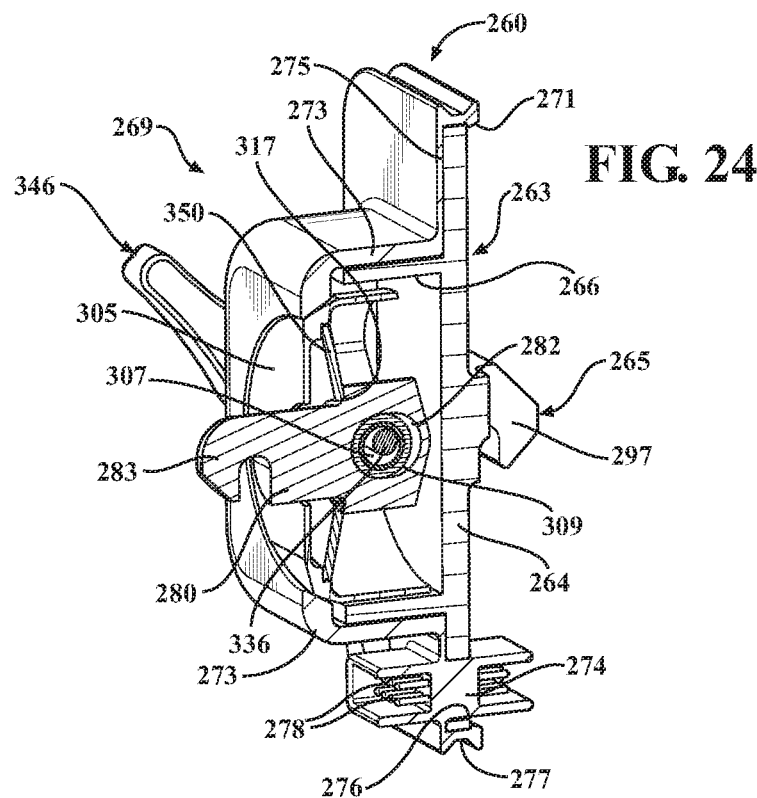
FIG. 24 is a cross-sectional perspective view of the alternative sterile barrier assembly (without drape)

The interface 260 includes a plurality of electrical terminals embedded in the cover 269, as shown in FIG. 24. In this embodiment, the electrical terminals are pins 278 that may be insert molded into the cover 269 of the interface 260. The pins 278 are located in a connector portion 274 of the cover 269. The connector portion 274 partially passes through an aperture 276 in the latch bracket 263. The connector portion 274 may be press fit into the aperture 276 to reduce the potential for contaminants to migrate through the interface 260. A peripheral seal (not shown) may also be present to seal against the connector portion 274 and the main wall 264 in the aperture 276 to further reduce the potential for contaminants to migrate through the interface 260. The pins 278 transfer electrical power/signals across the sterile barrier assembly 222.

Referring to FIGS. 18-20, the first mounting portion 224 includes a first catch 288. In this embodiment, the first catch 288 is a sliding catch plate. The first catch 288 defines a pair of spaced apertures 289 (FIG. 20). The first catch 288 is slidably disposed in the first body 242. The first body 242 includes a forward wall 285. A cover plate 293 is mounted to the forward wall 285 to define a catch guide recess 287. The first catch 288 slides in the catch guide recess 287.

One or more compression springs 291 biases the first catch 288 upwardly so that an upper edge of the first catch 288 contacts a downwardly facing edge of the forward wall 285 defining the catch guide recess 287. The compression springs 291 act between a lower edge of the first catch 288 and an opposing upwardly facing edge of the forward wall 285 defining the catch guide recess 287.

The forward wall 285 also defines a latch aperture 295 through which the latches 265 are able to engage the first catch 288. In the normal state, the apertures 289 are only partially aligned with the latch aperture 295, as shown in FIG. 20. Still, a large enough portion of the apertures 289 are exposed through the latch aperture 295 for the latches 265 to engage the first catch 288.

Each of the latches 265 has a head 297 that tapers to a front surface sized to fit within the exposed portion of the apertures 289. As the front surfaces of each head 297 moves into and through the exposed portion of the apertures 289, a tapered surface of the head 297 cams the first catch 288 downwardly against the bias of the compression springs 291 until the head 297 moves entirely through the apertures 289. Once the heads 297 have passed entirely through the apertures 289, the first catch 288 slides upwardly into a latch recess 299 defined by each of the heads 297 under the bias of the compression springs 291. This holds the latch bracket 263, and by extension the entire sterile barrier assembly 222, onto the first body 242.

This latch/catch arrangement allows the interface 260 to engage the first body 242 without requiring any tilting therebetween. In other words, the interface 260 can be pressed into engagement with the first body 242 by solely translational or linear movement of the interface 260. This further facilitates the engagement of the pins 278 into corresponding electrical connectors 251, 257 on the first body 242 and second body 246. It should be appreciated that the latches 265 and the first catch 288 could be reversed or that the latches 265 and the first catch 288 could be referred to as catches 265 and the first latch 288.

An actuator 301 is used to release the latch bracket 263 from the first body. The actuator 301 is fixed to the first catch 288. In this embodiment, the actuator 301 is U-shaped and can be actuated by pressing the actuator 301 downwardly to move the first catch 288 downwardly against the bias of the compression springs 291 so that the heads 297 of the latches 265 can be pulled back out through the apertures 289 and the latch aperture 295.

Referring to FIG. 19, with the interface 260 supported by the first body 242, the second body 246 is ready to engage the interface 260. A latch hook 283 is located to easily engage a second catch 306 fixed to the second body 246 (or could be referred to as the catch hook 283 and the second latch 306). The latch hook 283 is pivotally supported by the latch bracket 263. A torsion spring (not numbered in FIG. 26) biases the latch hook 283 into engagement with the second catch 306.

The second catch 306 is a D-shaped rod fixed to the second body 246 and shaped to engage the latch hook 283. The second body 246 is simply pressed onto the interface 260 until the latch hook 283 engages the second catch 306. More specifically, as the second body 246 is pressed onto the interface 260, the second catch 306 presses against a tapered face of of the latch hook 283 thereby urging the latch hook 283 to pivot upwardly against the bias of the torsion spring until a recess in the latch hook 283 aligns with the second catch 306 at which time the torsion spring urges the latch hook 283 over the second catch 306, as shown in FIG. 19. Now the mounting system 220 is ready to be preloaded and prepared for use. In this state, the mounting system 220 acts as a support mechanism to support the end effector EE on the robotic arm R prior to preloading.

Figure 27:
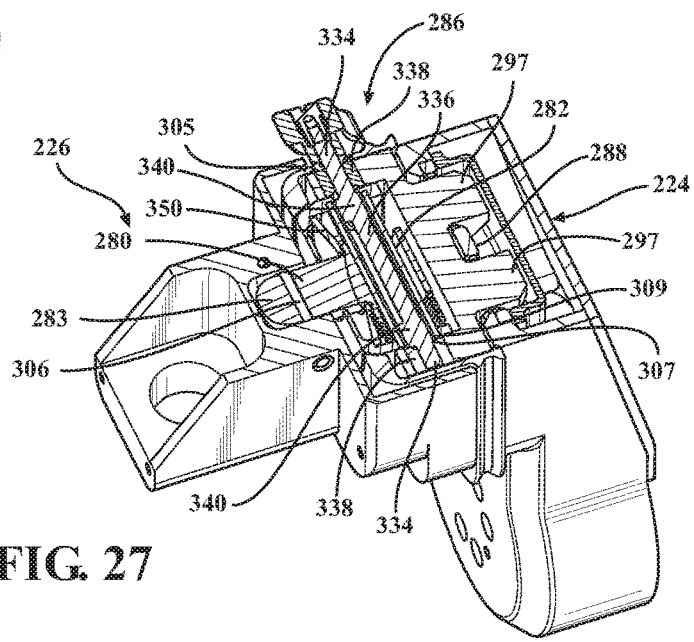
FIG. 27 is a cross-sectional perspective view of the alternative mounting system of FIG. 17.
Figure 28:
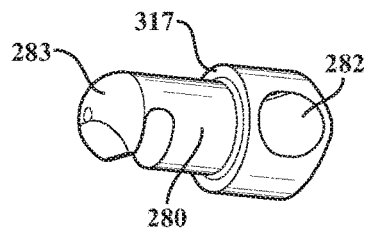
FIG. 28 is a perspective view of a load member.
Figure 29:
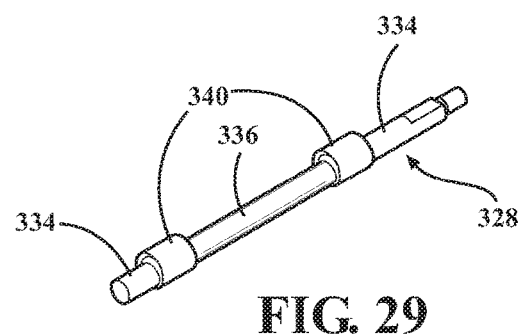
FIG. 29 is a perspective view of a cam shaft.
Figure 30:
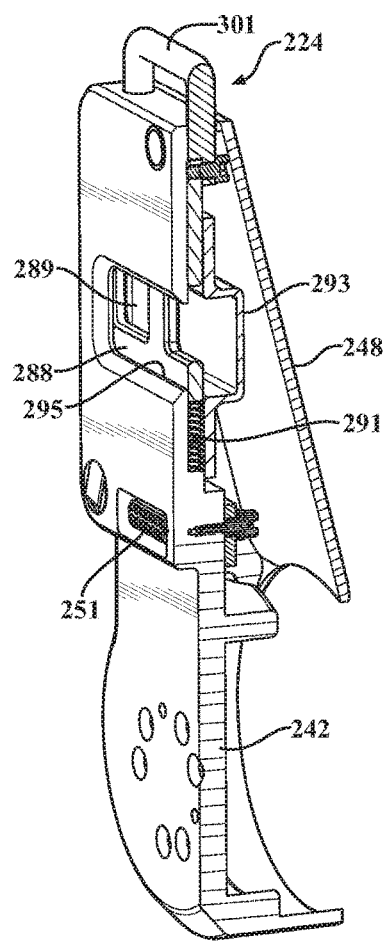
FIG. 30 is a cross-sectional perspective view of the first mounting portion.
Figure 31:
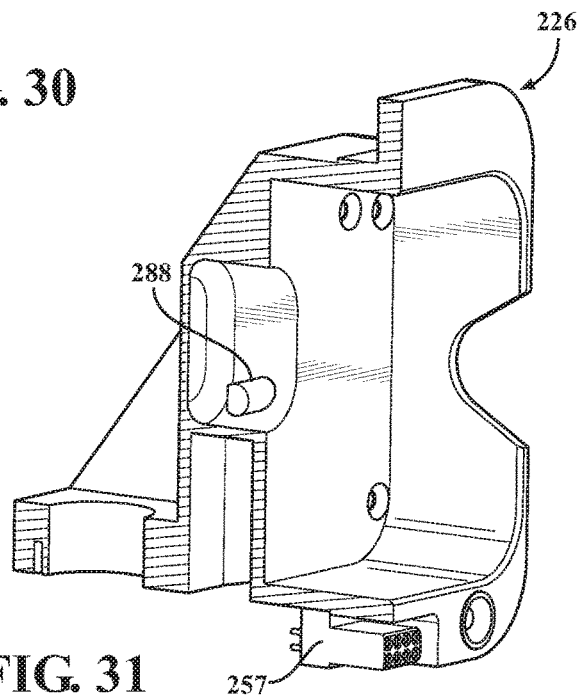
FIG. 31 is a cross-sectional perspective view of the second mounting portion.

Referring to FIGS. 25-27, a preloading mechanism 286 clamps the mounting portions 224, 226 together in position once they are brought together in approximate final orientation. A preloading element is located in the interface 260. In this embodiment, the preloading element is an elongated load member 280. The load member 280 is movably supported in the interface 260. The load member 280 has first and second ends. The load member 280 may be formed of stainless steel, Kevlar composite, or other suitably rigid materials. The load member 280 defines an aperture 282 near one end and the latch hook 283 adjacent the opposite end.

A preload force is applied to the load member 280. The preload force is sized to exceed anticipated loading through the kinematic coupling so that the kinematic coupling and associated properties are maintained.

The load member 280 is movably supported by the latch bracket 263. In particular, the load member 280 is able to move from an unloaded position to a loaded position relative to the latch bracket 263. In the unloaded position, the latch hook 283 is located to engage the second catch 306. In the loaded position, the load member 280 is urged toward the latch bracket 263 to load the mounting system 220.

The preloading mechanism 286 further includes a tensioner 318 (FIG. 26) and a spring cup 305 coupled to the tensioner 318. The tensioner 318 includes a cam shaft 328 that fits inside a pair of concentric inner and outer tubes 307, 309. The tubes 307, 309 are hollow and cylindrical. The tubes 307, 309 are fixed from translation relative to the spring cup 305 so that as the tubes 307, 309 move in translation, so does the spring cup 305.

The spring cup 305 defines a first cup opening 311 (FIG. 25) that is sized to receive the outer tube 309. Opposite the first cup opening 311, the spring cup 305 defines a spring cup counterbore 315 (FIG. 25) sized to receive the outer tube 309. The outer tube 309 may be press fit into the first cup opening 311 and the spring cup counterbore 315 so that the outer tube 309 is unable to rotate relative to the spring cup 305, or the outer tube 309 may be allowed to rotate therein but be fixed from moving in translation relative to the spring cup 305. The outer tube 309 passes through the aperture 282 of the load member 280.

The latch hook 283 protrudes beyond a central opening in the spring cup 305. The latch hook 283 also protrudes beyond a central opening in a top of the outer wall 273 to reach the second catch 306 of the second body 246. The spring cup 305 is sized so that the spring cup 305 is unable to pass through the central opening in the top of the outer wall 273. The spring cup 305 and outer wall 273 have chamfered surfaces configured to clear one another in the unloaded state when the latch hook 283 is released as described further below.

The cam shaft 328 is supported for rotation by the inner wall 266 of the latch bracket 263. The inner wall 266 defines a pair of throughbores 301 (FIG. 26). A pair of bushings 338 are press fit into the throughbores 301 and rotatably support outer cylindrical sections 334 of the cam shaft 328. As a result, the cam shaft 328 is able to rotate relative to the latch bracket 263 between tensioned and untensioned positions. The cam shaft 328 includes a pair of cam sections 340 separated by a middle cylindrical section 336. The cam sections 340 have an outer diameter slightly smaller than an inner diameter of the inner tube 307. The cylindrical sections 336 of the cam shaft 328 have a smaller diameter than the cam sections 340 thereby creating a camming action as the cam shaft 328 is rotated.

The inner and outer tubes 307, 309 each have a length less than a length across opposing sections of the inner wall 266 between the throughbores 301. As a result, the inner and outer tubes 307, 309 can move in translation relative to the inner wall 266. As the cam shaft 328 is rotated, the inner and outer tubes 307, 309 move under the cam action of the cam shaft 328 toward and away from the main wall 264. This movement provides the preloading needed to load the load member 280 once the latch hook 283 has engaged the second catch 306.

The tensioner 318 also includes a lever 346 rotatably fixed to the cam shaft 328. The lever 346 includes a boss 348 having a D-shaped bore to receive the D-shaped portion of the cam shaft 328 so that the cam shaft 328 rotates as the lever 346 rotates. A fastener (not numbered) engages a threaded end of the cam shaft 328 to secure the lever 346 to the cam shaft 328. The cam shaft 328 is rotated at least ninety degrees to move between the unloaded and loaded positions. Of course, other positions therebetween may place tension on the load member 280 and could be suitable for applying the desired preload force.

The lever 346 may be locked when the cam shaft 328 is placed in the desired position, e.g., the loaded position. In the loaded position, the preload tensile force is applied to the load member 280. By locking the lever 346 after applying the preload force, the preload force is continually applied during use of the robotic arm R and end effector EE to maintain the kinematic coupling. The preloading mechanism 286 transfers the preload force across the sterile barrier assembly 222 without piercing the barrier.

The tensioner 318 applies the preload force to the load member 280 through a conical disc spring 350, such as a Belleville spring. The disc spring 350 applies a force equal to the preload force to the load member 280. The disc spring 350 acts between the spring cup 305 and a shoulder 317 of the load member 280. In particular, as the lever 346 is rotated, the cam shaft 328 rotates and the cam sections 340 move the inner and outer tubes 307, 309, and by extension the spring cup 305, away from the latch hook 283 (now engaging the second catch 306). The inner and outer tubes 307, 309 are also able to move relative to the load member 280 by virtue of moving in the aperture 282, which is elongated to accommodate for such movement. The movement of the spring cup 305 relative to the load member 280 compresses the disc spring 350 and applies the preload force onto the load member 280 via the shoulder 317.

Since the balls 228 are aligned with the first and second plurality of receptacles 230, 232, 234, 236, 238, 240, once the preload force is applied, the balls 228 become seated in the receptacles 230, 232, 234, 236, 238, 240. Once seated, positions of the balls 228 are fixed and the positions of the first and second plurality of receptacles 230, 232, 234, 236, 238, 240 are fixed relative to one another. As a result, the first and second mounting portions 224, 226 are kinematically coupled together without piercing the sterile barrier assembly 222.

Release of the latch hook 283 is facilitated by urging the latch hook 283 upwardly away from the second catch 306. This is accomplished by rotating the lever 346 further counterclockwise when in the unloaded position. This movement causes the cam shaft 328 to interact with a second cup opening 313 defined in the spring cup 305 to pivot the spring cup 305 and the latch hook 283 to release the latch hook 283 from the second catch 306.

Figure 26A:
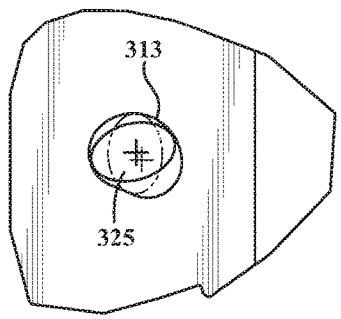
FIG. 26A is a close-up view taken from FIG. 26.

The second cup opening 313 is smaller than the outer tube 309, yet large enough to accommodate an eccentric portion 325 of the cam shaft 328. The second cup opening 313 has an eccentric shape as shown in FIG. 26A and is dimensioned so that in the unloaded position the eccentric portion 325 rests in the location indicated in solid lines in FIG. 26A. From this position, when the eccentric portion 325 is further rotated counterclockwise via lever 346, the eccentric portion 325 engages the spring cup 305 in a manner that causes pivoting of the spring cup 305. More specifically, since the eccentric portion 325 is constrained from further rotating counterclockwise given the dimensions of the second cup opening 313 (as viewed in FIG. 26A), further counterclockwise motion of the lever 346 pivots the spring cup 305 relative to the outer wall 273, and thereby moves the latch hook 283 upwardly away from the second catch 306. In the loaded position, the eccentric portion 325 rests in the location indicated by dashed lines in FIG. 26A.

FIG. 19 shows electrical power and/or other signal connections that can be made through the sterile barrier assembly 222. These connections employ the pins 278 embedded in the interface 260. These pins 278 electrically interconnect electrical connectors 251, 257 attached to the first and second mounting portions 224, 226.

In this embodiment, the first mounting portion 224 includes the first electrical connector 251. The first electrical connector 251 is able to float relative to the first body 242. The second mounting portion 226 includes the second electrical connector 257. The second electrical connector 257 also floats relative to the second body 246. When the first and second mounting portions 224, 226 are kinematically coupled together and preloaded, the electrical connectors 251, 257 receive the pins 278 so that power or other electrical signals can flow through the pins 278. Thus, power, communication signals, or other signals can be passed from the robotic arm R to the end effector EE and vice versa.

Figure 32:
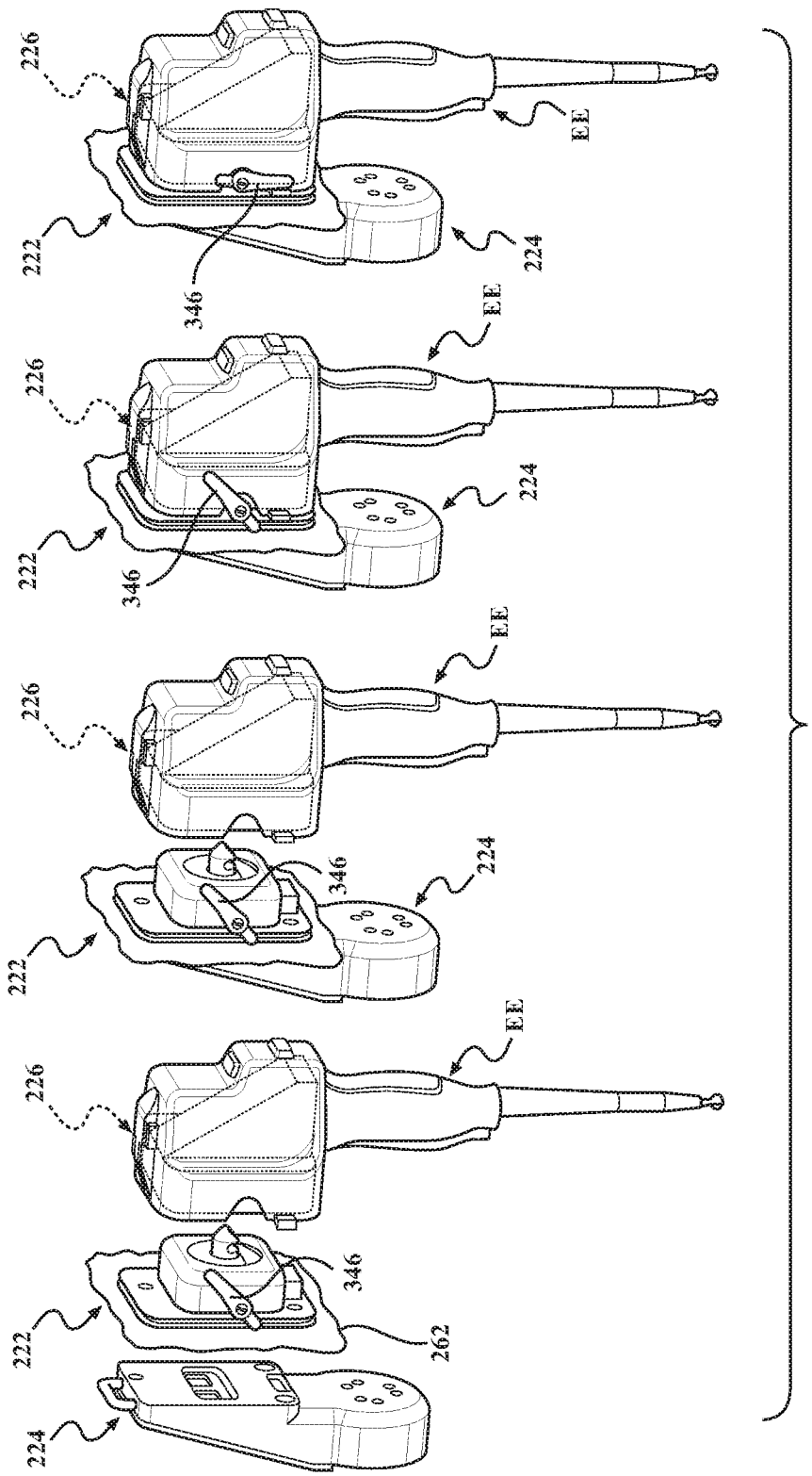
FIG. 32 illustrates the steps of mounting the alternative sterile barrier assembly onto a robotic arm and an end effector.
Figures 33, 35:
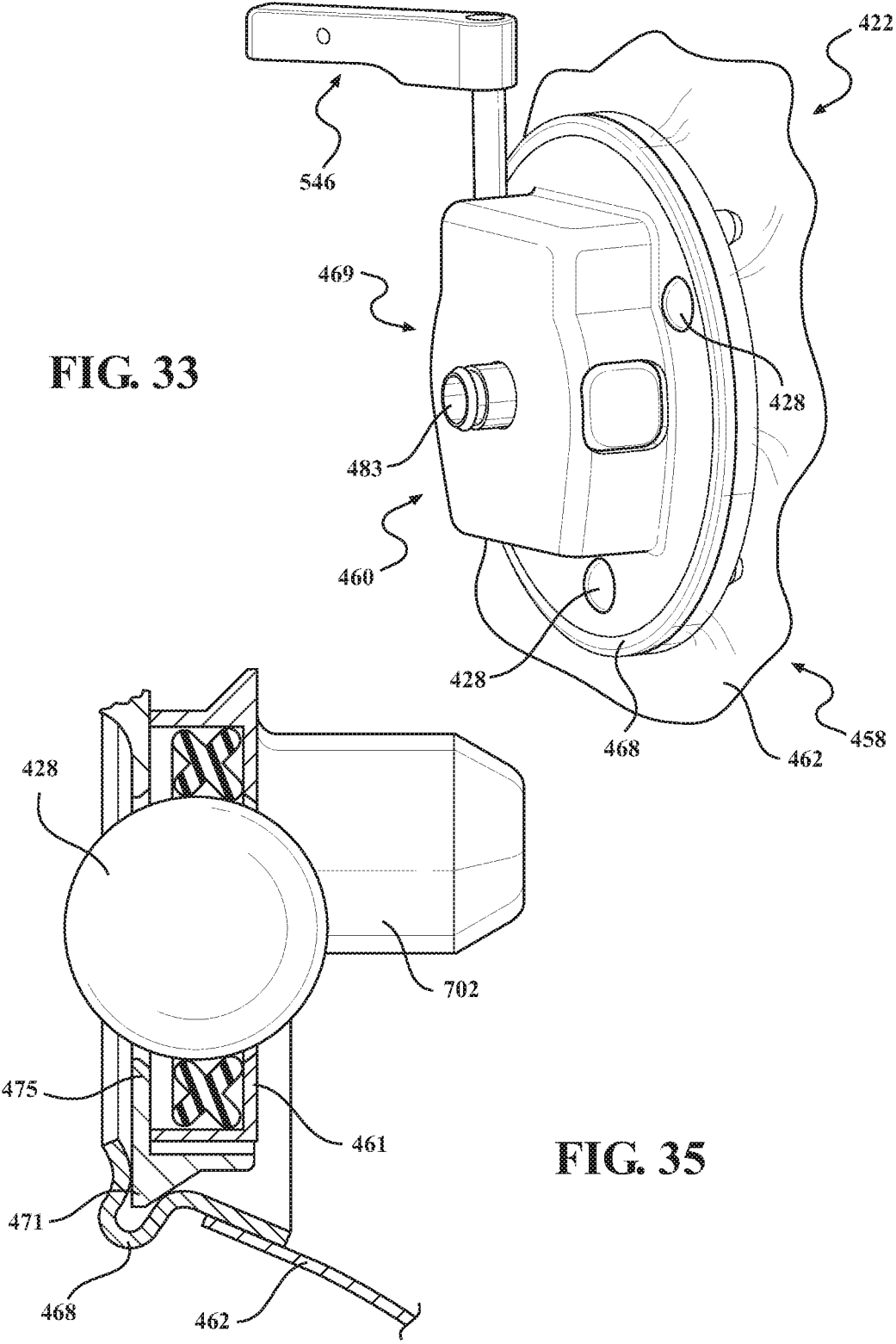
FIG. 33 is another alternative barrier assembly.
FIG. 35 is a close-up view of a drape of the alternative barrier assembly of FIG. 33.
Figure 34:
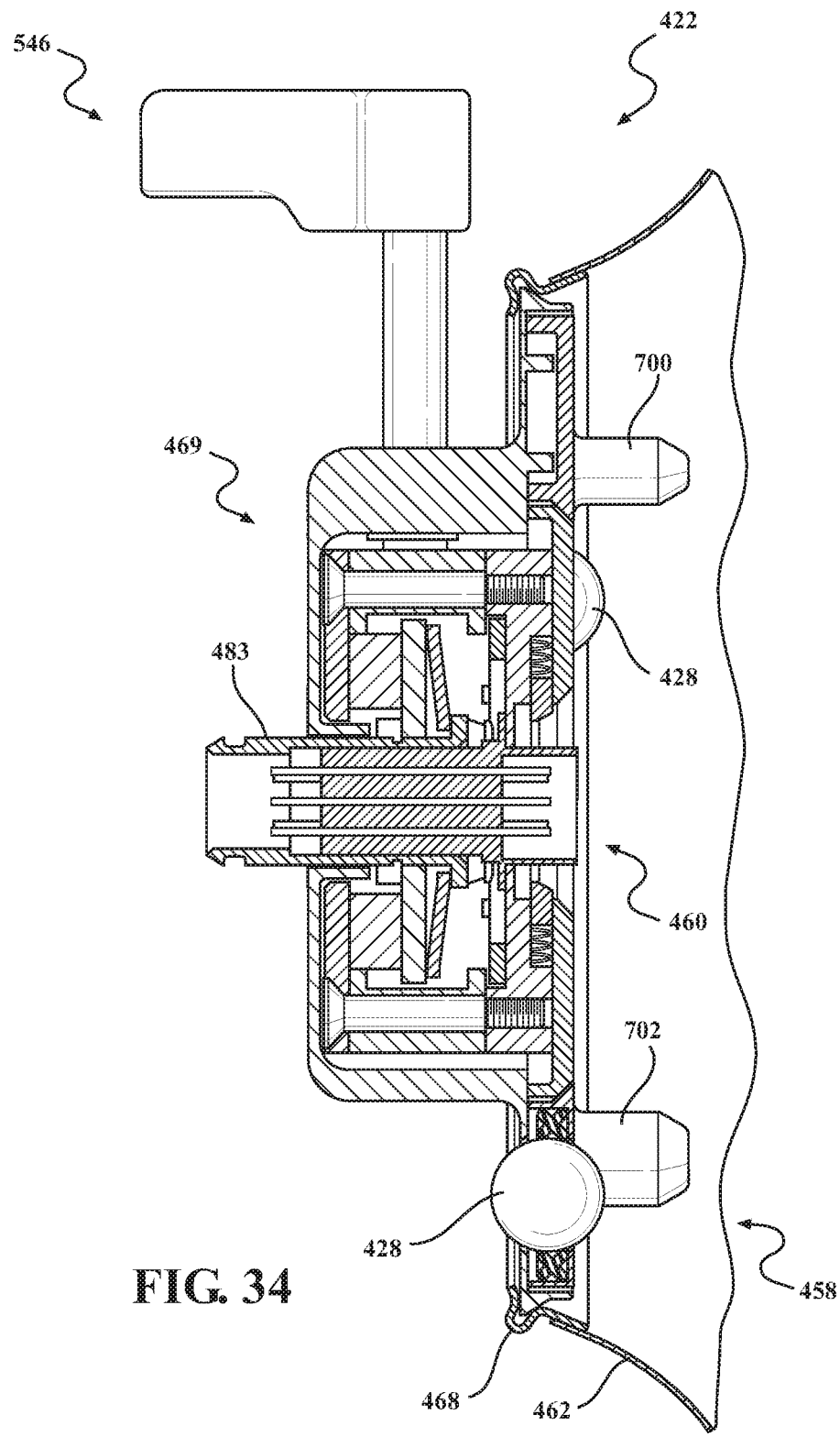
FIG. 34 is a cross-sectional view of the alternative barrier assembly of FIG. 33.

FIG. 32 shows the steps of attaching the sterile barrier assembly 222 first to the first mounting portion 224 (which is fixed to the robotic arm R), then attaching the second mounting portion 226 (shown in phantom integrated into the end effector EE) to the sterile barrier assembly 222, and then pivoting the lever 346 downwardly to load the mounting system 220 and apply the preload force necessary to maintain positioning between the first mounting portion 224 and the second mounting portion 226.

Referring to FIGS. 33-47, another alternative mounting system is shown for kinematically coupling the first and second surgical components (e.g., robotic arm R and end effector EE) using a sterile barrier assembly 422.

Referring to FIGS. 33-36, a plurality of kinematic couplers, similar to those of prior embodiments, are used to kinematically couple the end effector EE to the robot arm R. In this embodiment, the kinematic couplers are spherical balls 428. The balls 428 are seated in first and second pluralities of receptacles 432, 438 (one pair shown in FIG. 36). The receptacles 432, 438 are sized and shaped to receive the balls 428, as previously described. The first plurality of receptacles 432 are fixed to a first mounting portion 424 of the robot arm R and the second plurality of receptacles 438 are fixed to a second mounting portion 426 of the end effector EE.

Figure 36:
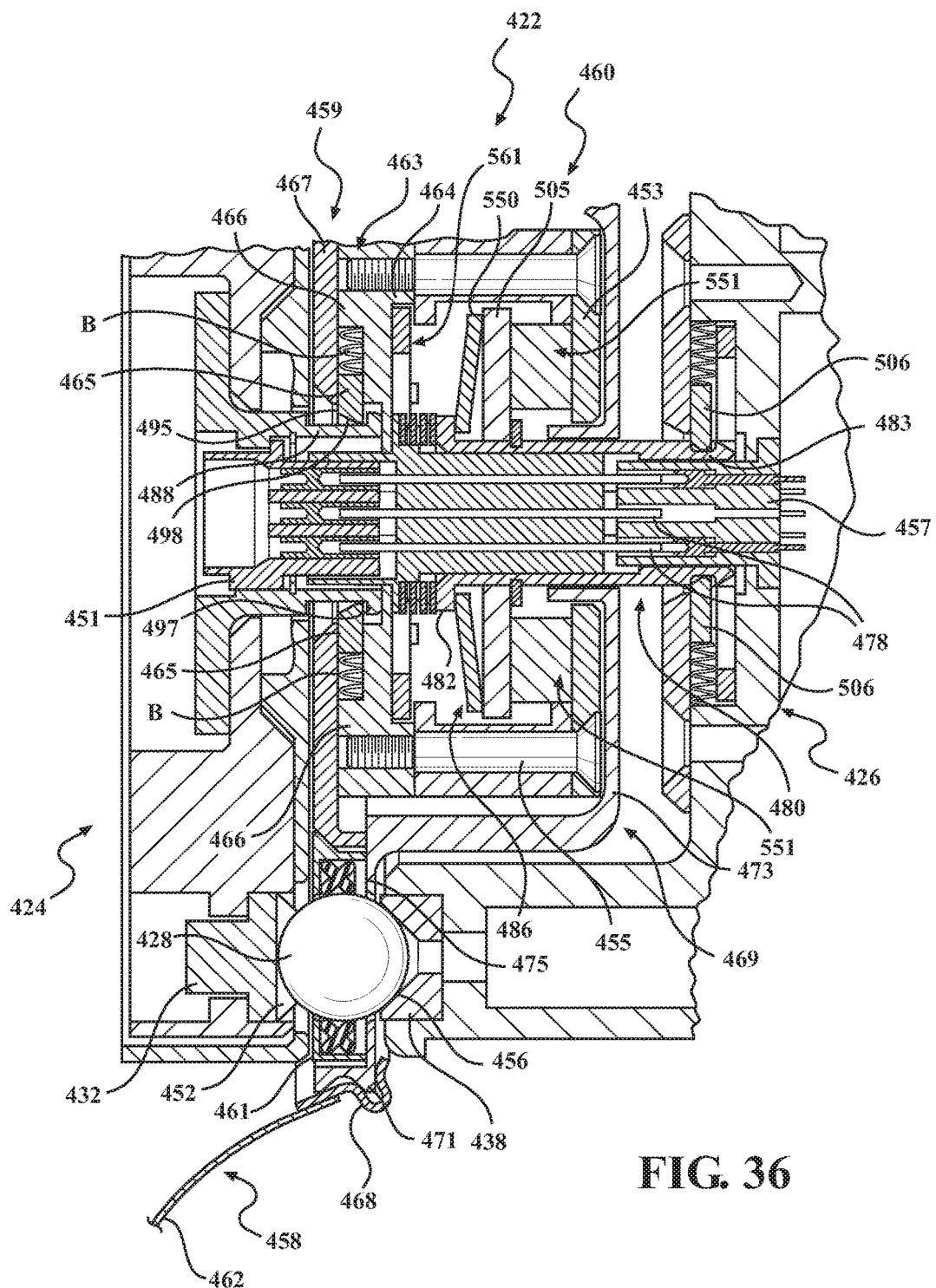
FIG. 36 is a cross-sectional view of another alternative mounting system incorporating the alternative barrier assembly of FIG. 33.

The first plurality of receptacles 432 includes three receptacles (only one shown in FIG. 36). Each of the first plurality of receptacles 432 has a pair of contact surfaces 452 provided by a V-shaped groove or gothic arch (also referred to as V-grooved receptacles). The second plurality of receptacles 438 includes three receptacles (only one shown in FIG. 36). Each of the second plurality of receptacles has a contact surface 456 with a conical configuration (i.e., cone receptacles). Three balls 428 are captured between corresponding, aligned pairs of the receptacles 432, 438.

When the mounting portions 424, 426 of the robot arm R and the end effector EE are brought together in approximate final orientation with the sterile barrier assembly 422 positioned therebetween, the balls 428 of the sterile barrier assembly 422 self-seat into the receptacles 432, 438 so that exactly six degrees of freedom are constrained, as described in the prior embodiments.

The sterile barrier assembly 422 includes a protective covering 458. The protective covering 458 includes an interface 460 and a drape 462 attached to the interface 460. The drape 462 has an interior surface and an exterior surface. The interior surface is placed adjacent to the robotic arm R during surgery. The drape 462 is formed of at least one of polyethylene, polyurethane, polycarbonate, or other suitable materials. The drape 462 may be directly attached to the interface 460 by ultrasonic welding, tape, adhesive, or the like.

In the embodiment shown, the drape 462 comprises a ring 468 that engages the interface 460. The ring 468 defines an opening. In the embodiment shown, the ring 468 is a snap-ring. A flaccid portion of the drape 462 is attached to the snap-ring 468 to surround the opening by ultrasonic welding, tape, adhesive, or the like. When draping the robot arm R, the snap-ring 468 (with flaccid portion attached thereto) is first snap-fit to the interface 460, prior to the interface 460 being mounted to the first mounting portion 424 of the robot arm R. The interface 460 fits into the opening in the snap-ring 468. Once the snap-ring 468 is snap-fit to the interface 460, the interface 460 is mounted to the first mounting portion 424 of the robot arm R. The drape 462 is attached to the interface 460 so that no perforations are present or are sealed, i.e., the drape 462 forms a continuous barrier with the interface 460 through the snap-ring 468 or other similar attachment mechanism. The drape 462 is absent in several Figures to better illustrate other components.

Figure 37:
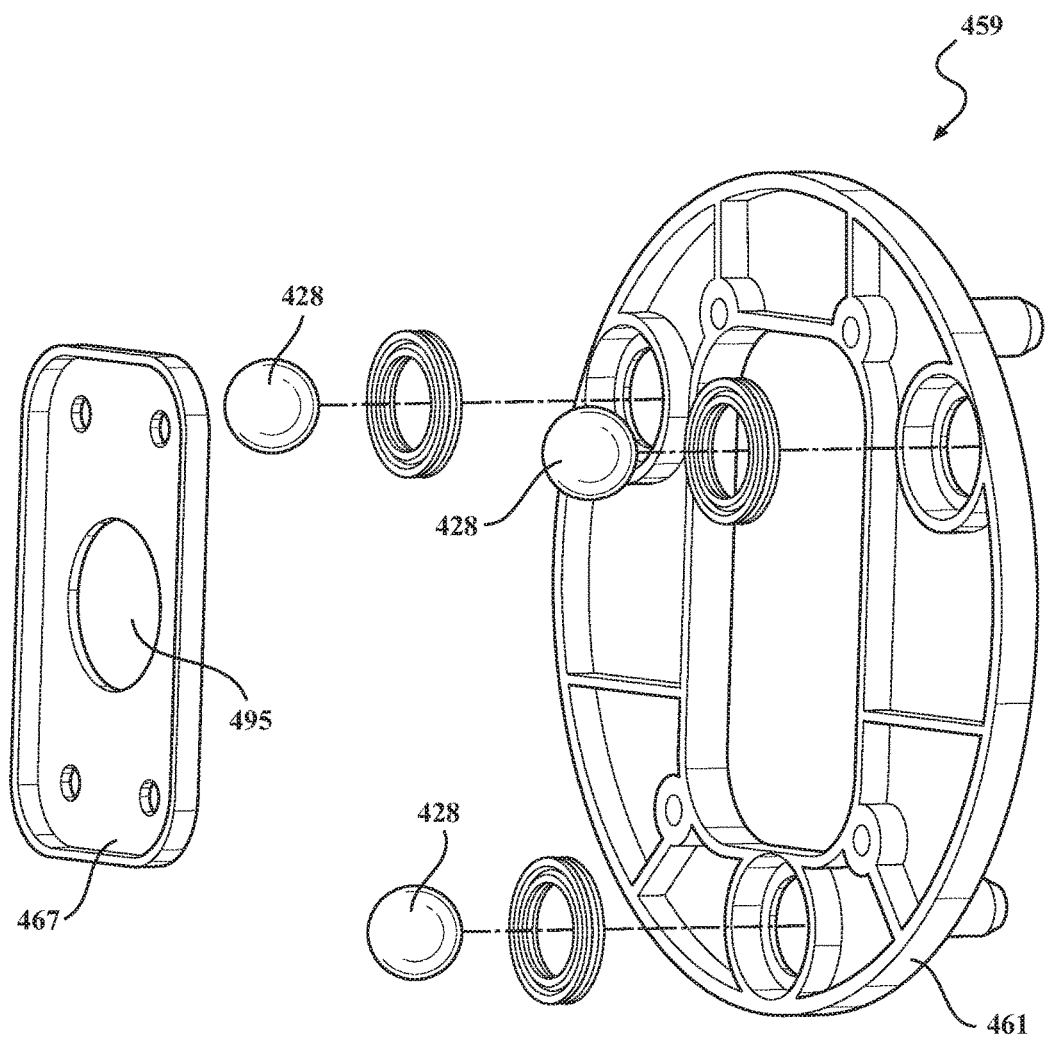
FIG. 37 is a perspective view of a back plate assembly of the alternative barrier assembly of FIG. 33.

Referring to FIGS. 36 and 37, in the embodiment shown, the interface 460 comprises a back plate assembly 459 that is secured to a cover 469. The back plate assembly 459 is formed of two separate components—a back ring plate 461 that is mounted by fasteners to the cover 469 and a back cover plate 467 that is captured between the back ring plate 461 and the cover 469.

Figure 38:
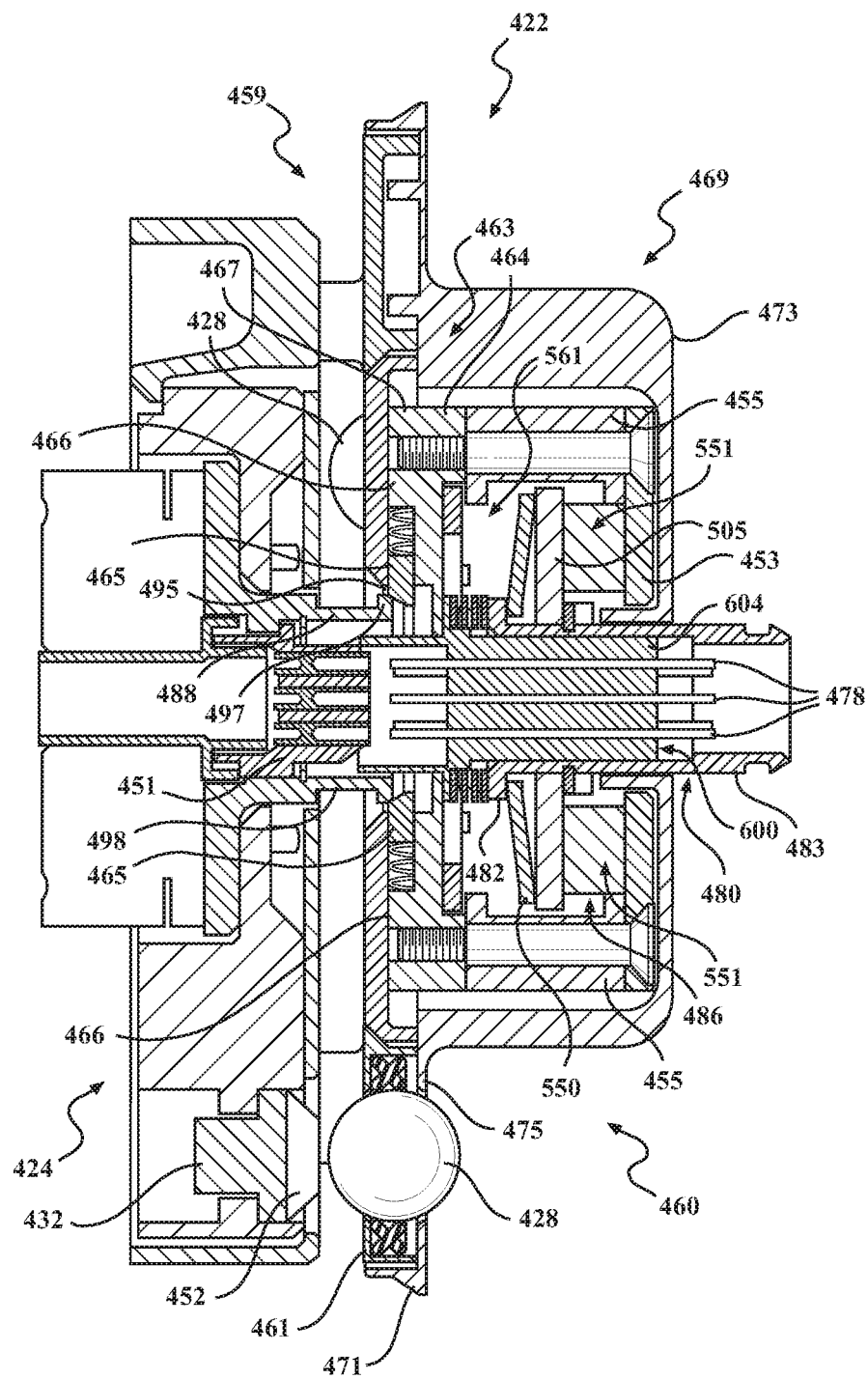
FIGS. 38 and 39 are cross-sectional views of the alternative barrier assembly of FIG. 33 showing connection to a first mounting portion of a robot arm.
Figure 39:
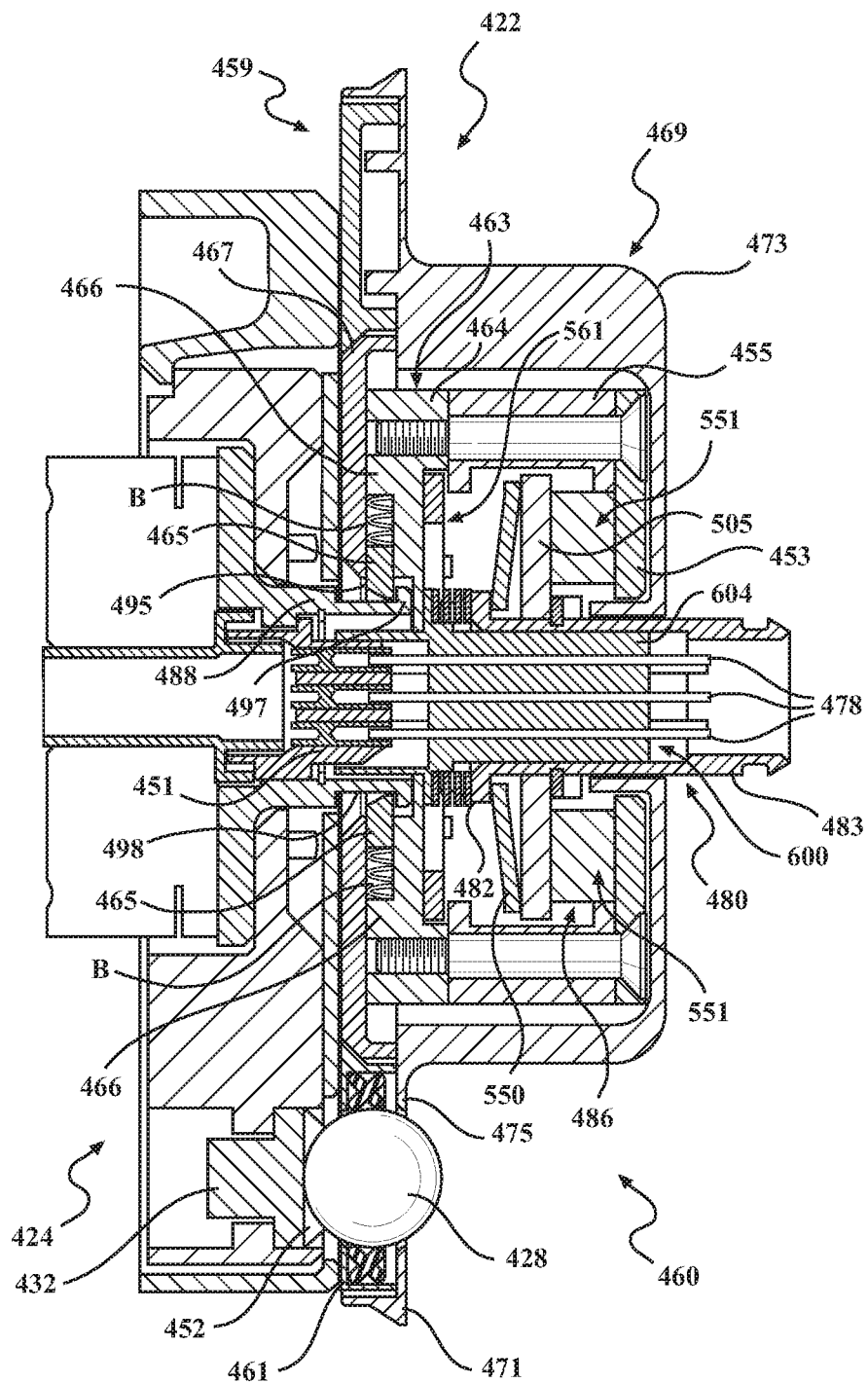

Referring to FIGS. 38 and 39, the interface 460 further includes a latch assembly 463. The latch assembly 463 includes a latch bracket 464 having spaced apart inner walls 466. A pair of latches 465 are held within a travel passage defined in the latch bracket 464 by the spaced apart inner walls 466.

The back cover plate 467 is fixed to the latch bracket 464 (e.g., via fasteners) and spaced from the latch bracket 464 to further define the travel passage for the latches 465. Each of the latches 465 are captured in the travel passage. A pair of biasing members B, such as springs, bias the latches 465 toward each other. The biasing members B act between the inner walls 466 and the latches 465. In this embodiment, the latches 465 are in the form of latch plates with arcuate recesses (see FIG. 46) to engage a first catch 488 of the first mounting portion 424 as described below.

The cover 469 has a peripheral lip 471. The cover 469 may be formed of injection molded plastic or metal. The peripheral lip 471 is secured around the back plate assembly 459. The cover 469 includes an outer wall 473 and a wall 475. The wall 475 extends from a base of the outer wall 473 to the peripheral lip 471. Seals (not shown) may be located between the cover 469 and the back plate assembly 459 to further enhance the barrier.

The interface 460 includes the balls 428 integrated therein. In this embodiment, the balls 428 are located in ball openings defined in the cover 469 and the back ring plate 461. The ball openings are sized so that a portion of each of the balls 428 protrudes out from the back ring plate 461 and the wall 475 of the cover 469 to engage the receptacles 432, 438. Seals that are X-shaped in cross-section hold the balls 428 in the ball openings and provide a sterile barrier around the balls 428, while still allowing the balls 428 lateral movement within the ball openings.

As described above, the balls 428 are arranged for receipt in the receptacles 432, 438 to kinematically couple the mounting portions 424, 426. The balls 428 are located so that the barrier remains unbroken between the back ring plate 461 and the balls 428 to reduce the potential for migration of contaminants through the interface 460. Thus, the drape 462 and interface 460 provide a continuous barrier to the migration of contaminants from the robotic arm R into the sterile field S.

In this embodiment, the balls 428 have polished, corrosion-resistant surfaces, so that under certain loads submicron repeatability in positioning the mounting portions 424, 426 can be achieved. The balls 428 may be formed of ceramic, stainless steel, or other suitable materials. The balls 428 may be formed of silicon carbide or tungsten carbide. The balls 428 may be precision machined to very tight tolerances, for example less than fifty millionths of an inch.

The first mounting portion 424 includes the first catch 488. In this embodiment, the first catch 488 is a catch post having a head 497 and a groove 498 proximal to the head 497. The latches 465 engage the first catch 488 in the groove 498. The back cover plate 467 defines a latch aperture 495 through which the head 497 is able to engage the latches 465. The head 497 is tapered to engage the latches 465. More specifically, the head 497 is tapered to spread apart the latches 465 from their normal positions (see FIG. 38). As the head 497 moves between the latches 465, a tapered surface of the head 497 spreads the latches 465 apart against the bias of the biasing members B until the head 497 moves entirely past the latches 465. Once the head 497 is past the latches 465, the latches 465 slide into the groove 498 to hold the sterile barrier assembly 422 onto the first mounting portion 424. Progressive engagement of the first catch 488 by the first pair of latches 465 is shown in FIGS. 38 and 39.

This latch/catch arrangement allows the interface 460 to engage the first mounting portion 424 without requiring any tilting therebetween. In other words, the interface 460 can be pressed into engagement with the first mounting portion 424 by solely longitudinal or linear movement of the interface 460.

Figure 40:
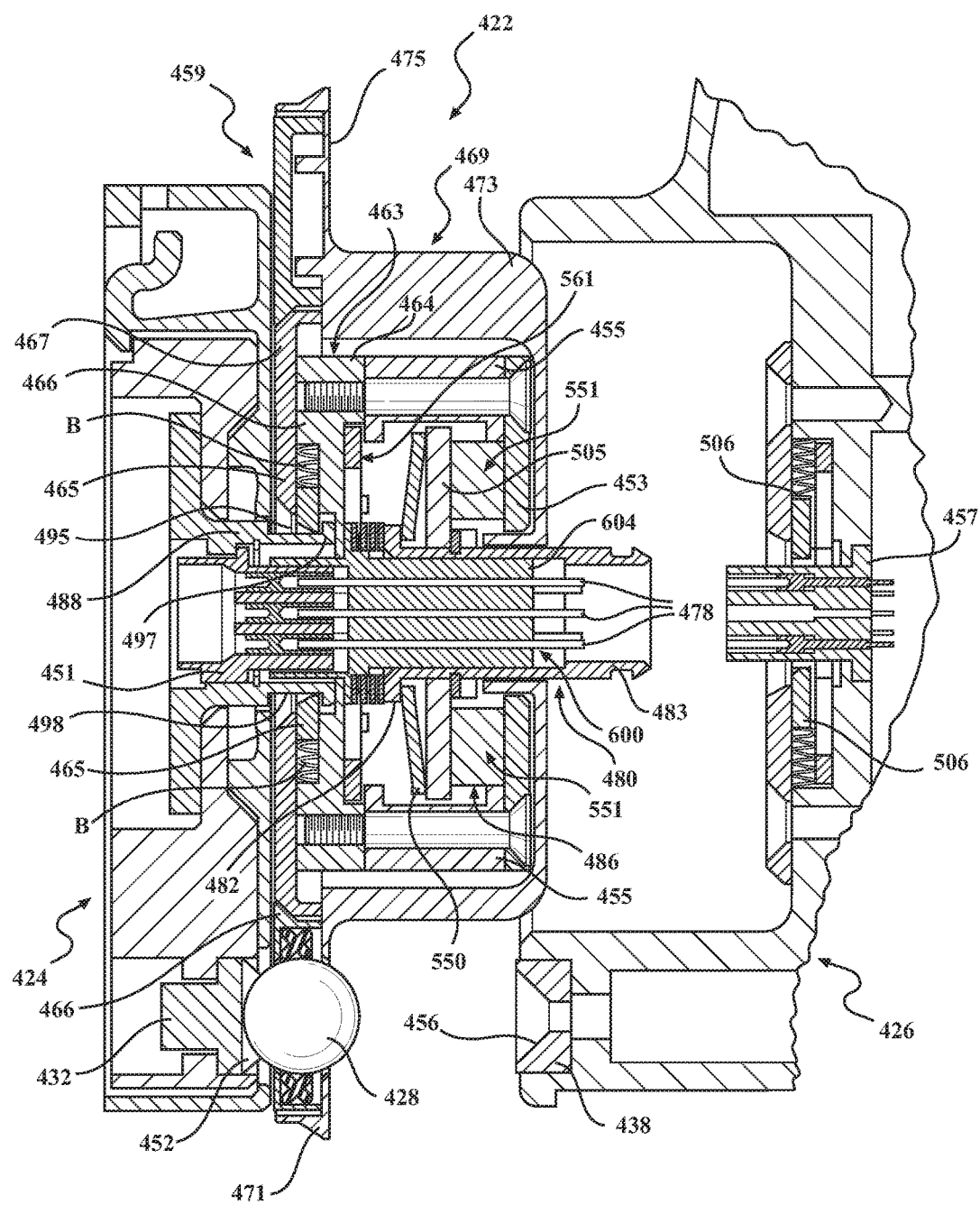
FIGS. 40 and 41 are cross-sectional views of the alternative barrier assembly of FIG. 33 showing connection to a second mounting portion of an end effector.
Figure 41:
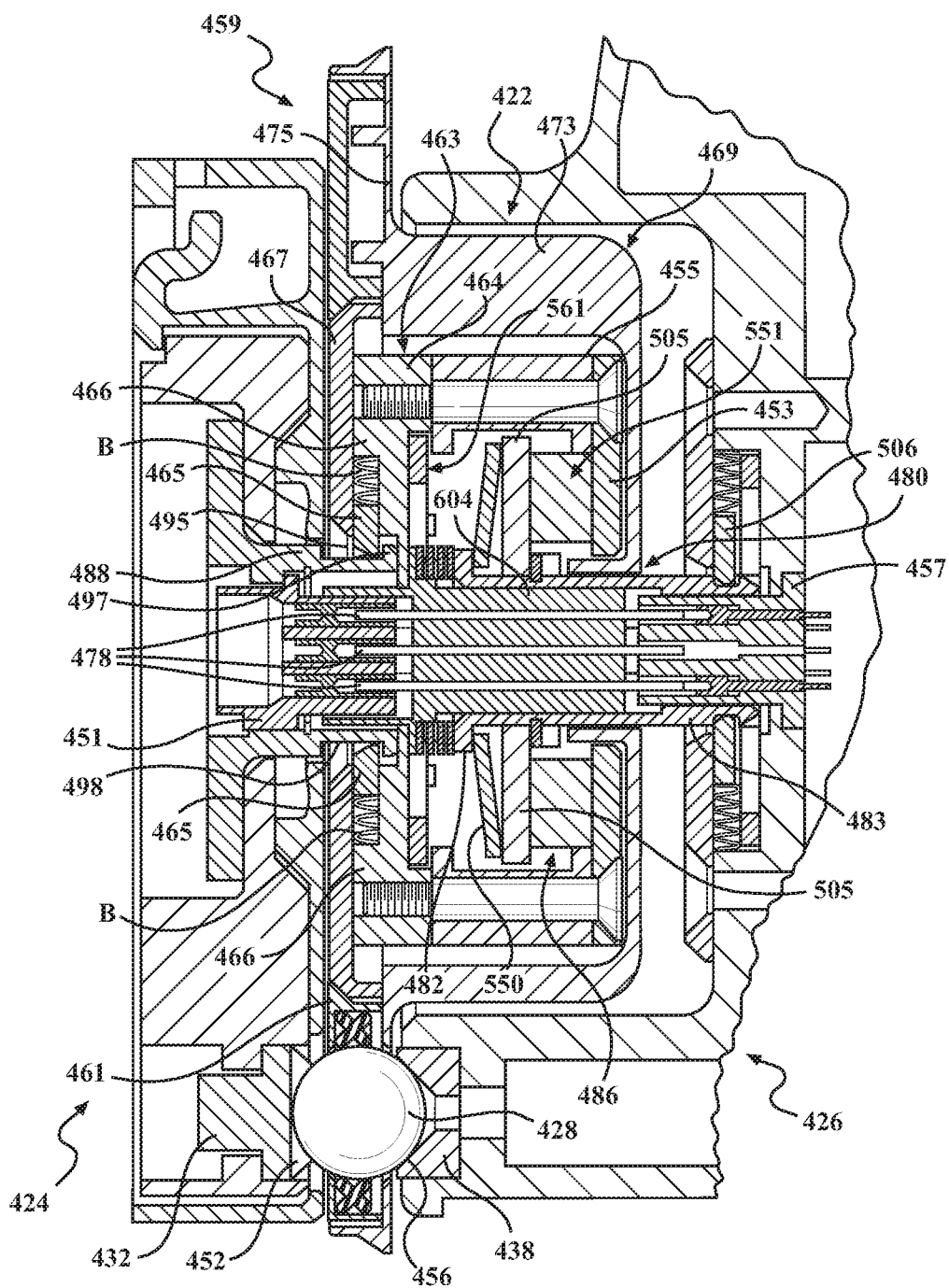
Figure 42:
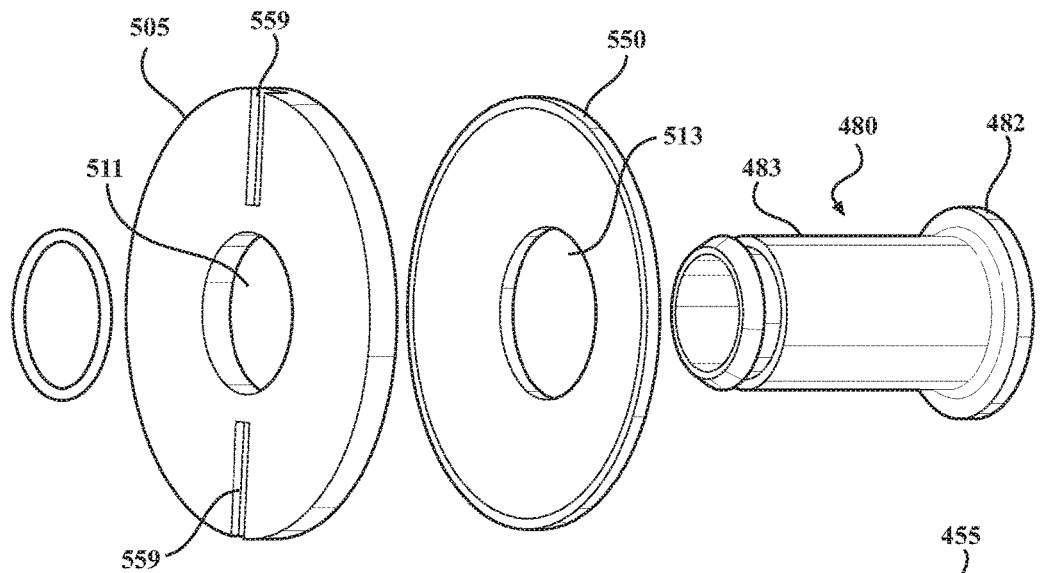
FIGS. 42 and 43 are exploded views of components of a preloading mechanism of the alternative barrier assembly of FIG. 33.
Figure 43:
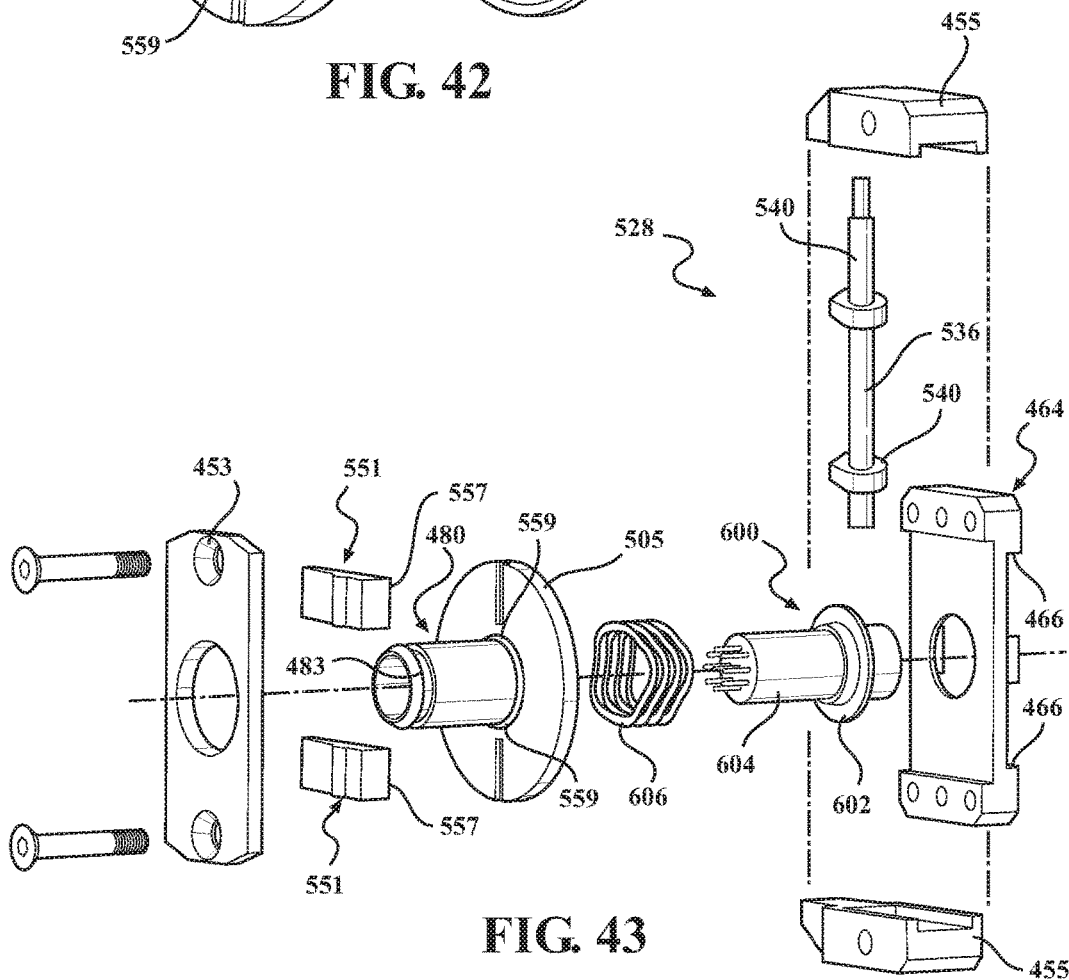

Referring to FIGS. 40 and 41, with the interface 460 supported by the first mounting portion 424, the end effector EE is now able to engage the interface 460. A second catch 483, similarly shaped to the first catch 488 is located to easily engage a second pair of latches 506 fixed to the second mounting portion 426. Operation and function of the second catch 483 and the second pair of latches 506 is similar to the first catch 488 and the first pair of latches 465 and will not be described in detail, but is progressively shown in FIGS. 40 and 41. The second mounting portion 426, which is attached to the end effector EE, is simply pressed onto the interface 460 until the second catch 483 engages the second pair of latches 506, as shown in FIG. 41. Now the mounting system is ready to be preloaded and prepared for use. In this state, the mounting system acts as a support mechanism to support the end effector EE on the robotic arm R prior to preloading.

Referring to FIGS. 36 and 42-45, a preloading mechanism 486 clamps the mounting portions 424, 426 together in position once they are brought together in approximate final orientation. A preloading element is located in the interface 460. In this embodiment, the preloading element is an elongated load member 480. The load member 480 is movably supported in the interface 460. The load member 480 has first and second ends. The load member 480 may be formed of stainless steel, Kevlar composite, or other suitably rigid materials. The load member 480 comprises a flange 482 near one end and the second catch 483 adjacent the opposite end.

A preload force is applied to the load member 480. The preload force is sized to exceed anticipated loading through the kinematic coupling so that the kinematic coupling and associated properties are maintained.

The load member 480 is movably captured between the cover 469 and the back plate assembly 459. In particular, the load member 480 is able to move from an unloaded position to a loaded position relative to the cover 469 and the back plate assembly 459. In the unloaded position, the second catch 483 is able to engage the second pair of latches 506. In the loaded position, the load member 480 is urged toward the back plate assembly 459 to load the mounting system.

Guide blocks 455 interconnect a cover plate 453 and the latch bracket 464. More specifically, the guide blocks 455 define bores through which fasteners pass to engage the latch bracket 464. The guide blocks 455 are arranged to space the cover plate 453 from the latch bracket 464. As a result, an internal space is provided in the interface 460 in which the load member 480 can be moved during preloading.

The preloading mechanism 486 further includes a spring plate 505 and a conical disc spring 550, such as a Belleville spring, disposed between the flange 482 of the load member 480 and the spring plate 505. The spring plate 505 defines a first opening 511 (see FIG. 42) that is sized to receive the load member 480. The disc spring 550 defines a second opening 513 that is also sized to receive the load member 480. A snap-ring secures the spring plate 505 and disc spring 550 to the load member 480.

The preloading mechanism 486 also includes a tensioner configured to, when actuated, urge the load member 480 toward the back plate assembly 459 to load the mounting system. The tensioner includes a cam shaft 528 supported for rotation relative to the cover 469 (see FIG. 44). The tensioner also includes a pair of tensioning members 551 (also referred to as lifters). The tensioning members 551 are located between the cover plate 453 and the spring plate 505. The cover plate 453 is fastened to the latch bracket 464 via fasteners.

The cam shaft 528 is supported for rotation by the guide blocks 455. As a result, the cam shaft 528 is able to rotate between tensioned and untensioned positions. The cam shaft 528 includes a pair of cam sections 540 separated by a middle cylindrical section 536. The cylindrical section 536 of the cam shaft 528 has a smaller diameter than the cam sections 540. The cam sections 540 create a camming action as the cam shaft 528 is rotated.

Figure 45:
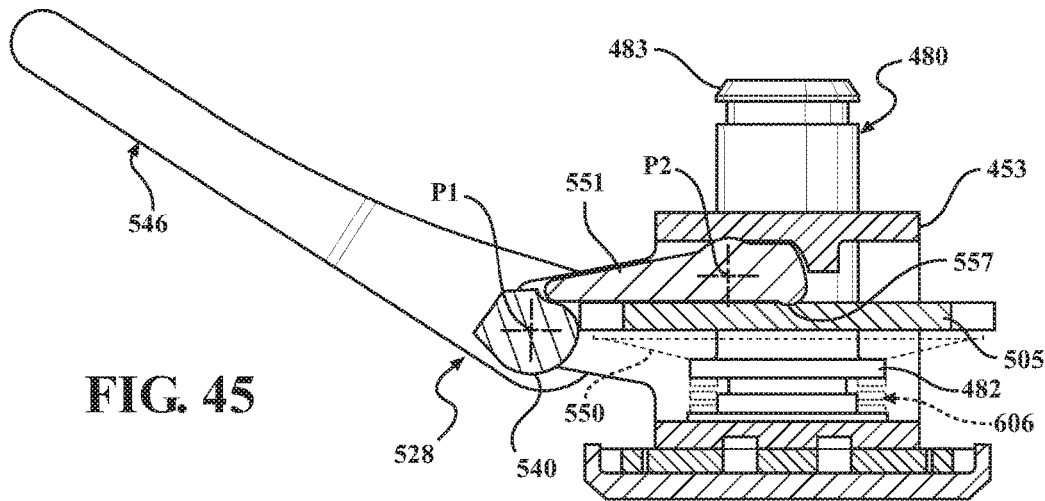
FIG. 45 is an illustration of the lever of FIG. 44 used to preload the alternative barrier assembly of FIG. 33.

As shown in FIG. 45, the tensioning members 551 (two in the embodiment shown) have first ends engaged by the cam shaft 528 and second ends that engage the spring plate 505. The second ends have rounded engagement sections 557 that sit in grooves 559 in the spring plate 505. As the cam shaft 528 is rotated about a pivot axis P1, the tensioning members 551 pivot about a pivot axis P2 while abutting the cover plate 453. This action pivots their second ends into the spring plate 505 to urge the spring plate 505 away from the cover plate 453. Owing to the rigid connection of the cover plate 453 to the latch bracket 464 and the latch bracket 464 to the back cover plate 467, the load member 480 moves toward the first catch 488 (which draws the second catch 483 toward the first catch 488), thereby providing the preloading needed to suitably secure the end effector EE to the robot arm R.

Figure 44:
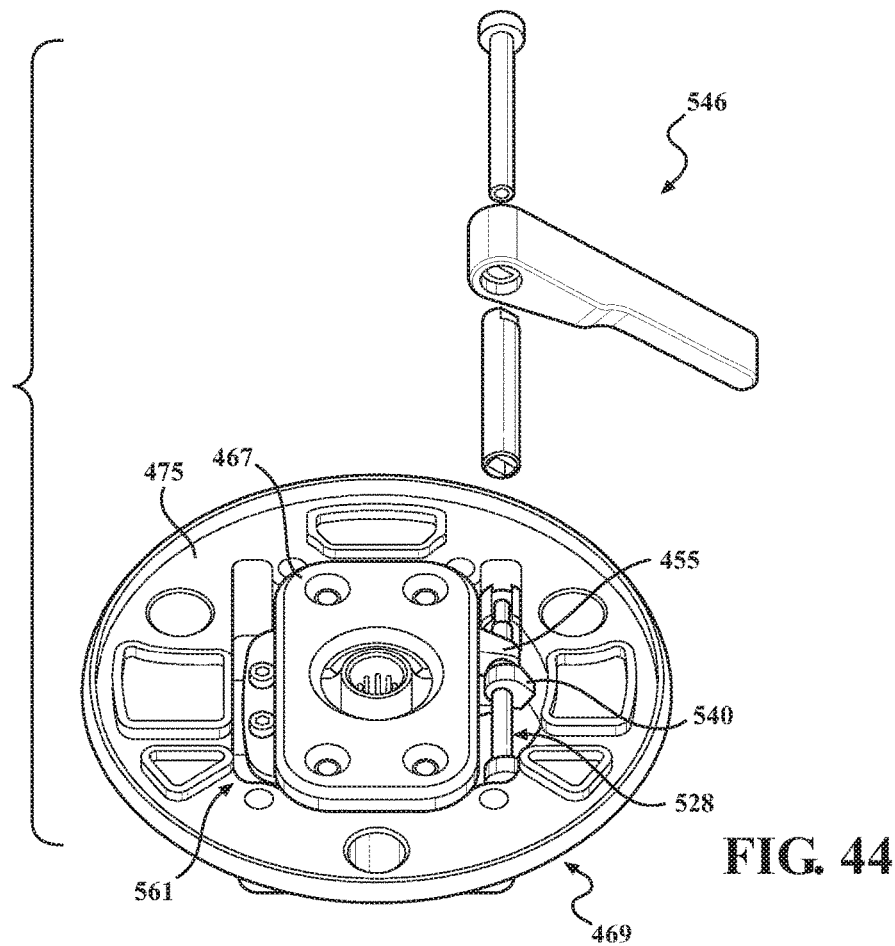
FIG. 44 is a partially exploded view of a lever of the alternative barrier assembly of FIG. 33.

As shown in FIGS. 44 and 45, the tensioner also includes a lever 546 rotatably fixed to the cam shaft 528. The lever 546 may be rotatably fixed to the cam shaft 528 through various types of engagements, e.g., a D-shaped bore to receive a D-shaped portion of the cam shaft 528, a coupler with geometric features so that the cam shaft 528 rotates as the lever 546 is rotated, etc. In the embodiment shown, a fastener (not numbered) secures the lever 546 to the cam shaft 528 via a coupler. The cam shaft 528 is rotated at least ninety degrees to move between the unloaded and loaded positions. Of course, other positions therebetween may place tension on the load member 480 and could be suitable for applying the desired preload force.

The lever 546 may be locked when the cam shaft 528 is placed in the desired position, e.g., the tensioned position. In the tensioned position, the preload tensile force is applied to the load member 480. By locking the lever 546 after applying the preload force, the preload force is continually applied during use of the robotic arm R and end effector EE to maintain the kinematic coupling. The preloading mechanism 486 transfers the preload force across the sterile barrier assembly 422 without piercing the barrier.

The tensioner applies the preload force to the load member 480 through the disc spring 550. The disc spring 550 applies a force equal to the preload force to the load member 480. The disc spring 550 acts between the spring plate 505 and the flange 482 of the load member 480. In particular, as the lever 546 is rotated, the cam shaft 528 rotates and the cam sections 540 pivot the tensioning members 551 about the pivot axis P2, and by extension, the spring plate 505 moves longitudinally away from the second catch 483 (which is engaging the second pair of latches 506). The movement of the spring plate 505 compresses the disc spring 550 and applies the preload force onto the load member 480 via the flange 482.

Since the balls 428 are already generally aligned with the receptacles 432, 438 before preloading, once the preload force is applied, the balls 428 become seated in the receptacles 432, 438. Once seated, positions of the balls 428 are fixed and the positions of the receptacles 432, 438 are fixed relative to one another. As a result, the mounting portions 424, 426 are kinematically coupled together without piercing the sterile barrier assembly 422.

Actuators, such as the push-button actuator 501 shown in FIG. 46, are used to manually separate the latches 465, 506 and release the catches 488, 483 so that the end effector EE can be removed from the interface 460 and the interface 460 can be removed from the robot arm R. Only the actuator 501 used to separate the first pair of latches 465 and release the first catch 488 will be shown and described in detail.

In the embodiment shown, the actuator 501 has a push button 560 fixed to a release frame 561. The release frame 561 is arranged with angled engagement surfaces 562 that engage pins 563 fixed to each of the first pair of latches 465. The pins 563 extend away from the latches 465 into openings 564 in the release frame 561. The openings 564 are partially defined by the angled engagement surfaces 562. The pins 563 extend on either side of the latch bracket 464 (see FIG. 46) so that the latches 465 are guided to move along the latch bracket 464 via the pins 563.

In a normal, unactuated state, the pins 563, by virtue of the latches 465 being biased toward one another by the biasing members B, are seated and constrained at one end of the openings 564. The actuator 501 can be actuated by pressing the push button 560, which moves the release frame 561 laterally across the latches 465, as shown by the arrow A1. The release frame 561 is constrained to this lateral motion by being captured in a slide pocket in the latch bracket 464. Owing to this lateral motion of the release frame 561 and the latches 465 being constrained from similar lateral movement by the pins 563, the angled surfaces 562 urge the pins 563 of each of the latches 465 away from each other, thereby separating the latches 465 in the direction shown by arrows A2 against the bias of the biasing members B. As a result, the latches 465 are disengaged from the first catch 488 (not shown in FIG. 46) and the interface 460 can be removed from the first mounting portion 424.

FIGS. 38-41 shows electrical power and other signal connections that can be made through the sterile barrier assembly 422. In this embodiment, the interface 460 includes a plurality of electrical terminals embedded in a carrier 600 disposed centrally in the cover 469. In this embodiment, the electrical terminals are pins 478 that may be insert molded into the carrier 600 of the interface 460. The pins 478 transfer electrical power/signals across the sterile barrier assembly 422. These pins 478 electrically interconnect electrical connectors 451, 457 attached to the mounting portions 424, 426.

In this embodiment, the first mounting portion 424 includes the first electrical connector 451. The second mounting portion 426 includes the second electrical connector 457. When the mounting portions 424, 426 are coupled together and preloaded, the electrical connectors 451, 457 receive the pins 478 so that power and other electrical signals can flow through the pins 478. Thus, power, communication signals, or other signals can be passed from the robotic arm R to the end effector EE and vice versa. The electrical connectors 451, 457 can be keyed to the carrier 600 via a key/channel type interface or can be properly oriented by any suitable feature.

In the embodiment shown, the carrier 600 comprises a flange 602 (see FIG. 43) and a cylindrical body 604 extending from the flange 602 to support the pins 478. The cylindrical body 604 is sized to fit within a cylindrical passage through the load member 480. A wave spring 606 is located between the flange 602 of the carrier 600 and the flange 482 of the load member 480. The wave spring 606 helps to maintain a position of the carrier 600 with respect to the electrical connectors 451, 457, i.e., by preventing movement of the carrier 600 when the load member 480 moves to the unloaded position, which might otherwise occur due to frictional engagement between the cylindrical body 604 in the cylindrical passage of the load member 480. The wave spring 606 also assists in returning the load member 480 to its unloaded position to engage the end effector EE. The wave spring 606 is also used to keep the tensioning members 551 in grooves in the cover plate 453 and in the grooves 559 in the spring plate 505.

Referring to FIGS. 47A and 47B, the back ring plate 461 of the interface 460 further includes gross alignment features for aligning the interface 460 with the first mounting portion 424. In particular, the first mounting portion 424 defines corresponding mating features for receiving the alignment features. In the embodiment shown, the alignment features comprise posts 700, 702 extending rearwardly from a rear surface of the back ring plate 461 to engage openings 704, 706 in the first mounting portion 424. The posts 700, 702 include a first pair of posts 700 and a second pair of posts 702 arranged on the back ring plate 461 opposite the first pair of posts 700. The first pair of posts 700 are aligned in a plane, while the second pair of posts 702 are angled relative to one another, e.g., they are misaligned. The second pair of posts 702 are also wider than the first pair of posts 700.

The openings 704, 706 comprise a first pair of openings 704 sized and shaped to receive the first pair of posts 700 and a second pair of openings 706 sized and shaped to receive the second pair of posts 702. The openings 704, 706 are sized and spaced to receive the respective posts 700, 702 with a small tolerance, e.g., to facilitate gross positioning. Still, the second pair of posts 702 are sized so that they are unable to fit in the first pair of openings 704 and the first pair of posts 700 are aligned so that they are unable to fit in the second pair of openings 706. Owing to the spacing/arrangement of the posts 700, 702 and the openings 704, 706, the interface 460 is only able to be grossly fitted onto the first mounting portion 424 in one orientation. The gross positioning also helps to align the electrical connections described above prior to fully engaging the first catch 488 with the latches 465.

When the balls 28, 228, 428 are made of an electrically insulating material such as ceramic, the sterile barrier assembly 22, 222, 422 can be used as the electrical isolation needed to comply with electrical safety requirements.

The balls 28, 228, 428 may provide three electrical contacts or terminals if they are made of a conductive material. In such a case, the sterile barrier assembly 22, 222, 422 could still be used as the electrical isolation if the interfacing feature of the kinematic coupling is made out of electrically insulating material.

One or more of the balls 28, 228, 428 may have optically transparent portions defined therethrough for transmitting data. The optically transparent portions may include throughbores filled with transparent plastic material or other material to maintain the barrier.

The kinematic couplers may have spherical and/or cylindrical segments in other embodiments.

The first mounting portion 24, 224, 424 may be a separate part that is rigidly connected to linkage L1 of the robotic arm R. The second mounting portion 26, 226, 426 may be a separate part that is rigidly connected to a handpiece H of the end effector EE. In other embodiments, the first mounting portion 24, 224, 424 may be integrated into the one or more linkages of the robotic arm R and the second mounting portion 26, 226, 426 may be integrated into the handpiece of the end effector EE. The mounting portions 24, 224, 424, 26, 226, 426 may be formed of hardened steel, stainless steel or other rigid materials.

The robotic arm R may move the end effector EE in one or more degrees of freedom, including five or six degrees of freedom. The end effector EE may include a surgical tool for milling tissue such as a milling bur for milling bone to receive an implant.

Examples of a robotic arm and end effector that can be outfitted with the first and second mounting portions 24, 224, 424, 26, 226, 426 are described in U.S. patent application Ser. No. 13/958,070, filed on Aug. 2, 2013, entitled, "Surgical Manipulator Capable of Controlling a Surgical Instrument in Multiple Modes", hereby incorporated by reference.

The first plurality of receptacles may include three V-grooved receptacles. The three balls 28, 228, 428 would then self-center into three V-shaped grooves of the three V-grooved receptacles so that each ball 28, 228, 428 is contacting two surfaces of the V-shaped grooves at two contact points. As a result, the balls 28, 228, 428 make contact with the three V-grooved receptacles at a total of six contact points to constrain six degrees of freedom, i.e., each V-shaped groove constrains two degrees of freedom, thereby determinately orienting all six degrees of freedom between the first and second mounting portions. The first and second mounting portions are then clamped in this position with the preloading mechanism as previously described.

The first plurality of receptacles and the second plurality of receptacles may each include three V-grooved or gothic arch shaped receptacles so that exactly six contact points are made between contact surfaces of the first plurality of receptacles and the kinematic couplers and between contact surfaces of the second plurality of receptacles and the kinematic couplers.

The cone receptacles may be simplified by being replaced with three blocks having planar surfaces circumferentially equally spaced from one another and arranged at an angle approximating the cone angle. In this embodiment, the ball 28, 228, 428 seats within the three planar surfaces just like being seated in the cone, but contact is made at three contact points with the three planar surfaces.

One or more of the first plurality of receptacles and/or the second plurality of receptacles may comprise magnets to magnetically engage the balls in the receptacles. For instance, the first plurality of receptacles may comprise magnets to hold the balls to the first mounting portion until the second mounting portion is clamped to the first mounting portion. Similarly, the first mounting portion, having the contact surfaces of the receptacles integrated therein for kinematic coupling, could comprise magnets to hold the balls against the contact surfaces in the first mounting portion until the second mounting portion engages the first mounting portion.

The sterile barrier assembly 22, 222, 422 may be disposable. In other embodiments, the interface 60, 260, 460 may comprise a separate field sterilizable assembly and can be re-usable. In this version, only the drape 62, 262, 462 is disposable. In that case, there could be an adhesive tape, elastic seal, snap-ring, or mechanical clamping area of the drape 62, 262, 462 to seal to the interface 60, 260, 460 or features could be designed on the interface 60, 260, 460 to seal/clamp onto the drape 62, 262, 462. Forming the balls 28, 228, 428 out of hard ceramic such as silicon carbide may minimize wear issues associated with reusing the balls 28, 228, 428.

The protective covering 58, 258, 458 may include the drape 62, 262, 462 without the interface 60, 260, 460 in which case the balls 28, 228, 428 would be placed in openings in the drape 62, 262, 462 with the drape 62, 262, 462 being sealed to the balls 28, 228, 428. In other words, the balls 28, 228, 428 would be integrated into the drape 62, 262, 462 directly. In this instance, the robotic arm R could be configured to position the first plurality of receptacles 30, 32, 34, 230, 232, 234, 432 so that they lie in a generally horizontal plane so that the balls 28, 228, 428 can be placed in the first plurality of receptacles 30, 32, 34, 230, 232, 234, 432 and held there by gravity until installation of the sterile barrier assembly is complete.

Additional elastic straps or bungee cords may be attached to the interface and configured to releasably engage posts or other features on the first mounting portion to further initially support the sterile barrier assembly when initially attaching the sterile barrier assembly to the first mounting portion, e.g., after inserting the load bar 80 into the load bar slot 104 of the receiver 100.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A sterile barrier assembly for establishing a barrier between first and second surgical components, said sterile barrier assembly comprising:
   a protective covering having a plurality of kinematic couplers configured to provide a kinematic coupling between the first and second surgical components through said protective covering to constrain exactly six degrees of freedom of movement between the surgical components.

2. The sterile barrier assembly of claim 1, further being coupled to:
   a first mounting portion associated with the first surgical component;
   a second mounting portion associated with the second surgical component; and
   wherein the plurality of kinematic couplers are further configured to engage the mounting portions and to provide the kinematic coupling between the mounting portions through the protective covering to constrain six degrees of freedom of movement between the surgical components.

3. The sterile barrier assembly of claim 2 including a preloading mechanism having a preloading element, said preloading mechanism configured to clamp said mounting portions together through said protective covering.

4. The sterile barrier assembly of claim 3 wherein said preloading mechanism includes a tensioner operatively coupled to said preloading element for tensioning said preloading element and clamping said mounting portions together.

5. The sterile barrier assembly of claim 4 wherein said tensioner includes a cam shaft and a lever rotatably fixed to said cam shaft, said cam shaft rotatable between tensioned and untensioned positions.

6. The sterile barrier assembly of claim 3 wherein said preloading element includes a load member.

7. The sterile barrier assembly of claim 3 wherein said preloading mechanism includes one of a first catch or a first latch associated with said first mounting portion and one of a second catch or a second latch associated with said second mounting portion.

8. The sterile barrier assembly of claim 2 wherein said first mounting portion includes a first plurality of contact surfaces for engaging said plurality of kinematic couplers and said second mounting portion includes a second plurality of contact surfaces for engaging said plurality of kinematic couplers, said contact surfaces shaped to cooperate with said plurality of kinematic couplers to constrain the six degrees of freedom of movement between the surgical components.

9. The sterile barrier assembly of claim 8 wherein said first mounting portion includes a first plurality of receptacles having said first plurality of contact surfaces and said second mounting portion includes a second plurality of receptacles having said second plurality of contact surfaces.

10. The sterile barrier assembly of claim 8 wherein said first plurality of contact surfaces are configured to provide only six contact points with said plurality of kinematic couplers.

11. The sterile barrier assembly of claim 8 wherein each of said second plurality of contact surfaces have conical configurations.

12. The sterile barrier assembly of claim 2 including a support mechanism for supporting said protective covering on said first mounting portion when coupling the first and second surgical components.

13. The sterile barrier assembly of any of claim 2, wherein said first mounting portion is associated with a robotic arm and said second mounting portion is associated with an end effector.

14. The sterile barrier assembly of claim 1 wherein said protective covering includes an interface and a drape attached to said interface, said interface including said plurality of kinematic couplers integrated therein.

15. The sterile barrier assembly of claim 14 wherein each of said plurality of kinematic couplers are arranged to laterally move relative to one another.

16. The sterile barrier assembly of claim 14 wherein said interface includes a preloading element for preloading the kinematic coupling between the surgical components.

17. The sterile barrier assembly of claim 14 wherein said interface includes a plurality of electrical terminals.

18. The sterile barrier assembly of claim 14 wherein said drape comprises a ring defining an opening for receiving said interface and a flaccid portion attached to said ring.

19. The sterile barrier assembly of claim 14 wherein said protective covering includes a support member for supporting said protective covering on the first surgical component during installation on the first surgical component.

20. The sterile barrier assembly of claim 14 wherein said interface comprises at least one of a first latch or a first catch for engaging the first surgical component and at least one of a second latch or a second catch for engaging the second surgical component.

21. The sterile barrier assembly of claim 14 wherein said plurality of kinematic couplers are further defined as a plurality of balls.

22. The sterile barrier assembly of claim 21 wherein said plurality of balls are further defined as three balls configured to constrain the six degrees of freedom of movement between the surgical components.

23. The sterile barrier assembly of claim 21 wherein said balls comprise ceramic.

24. The sterile barrier assembly of claim 21 wherein said balls comprise at least one of silicon carbide or tungsten carbide.

25. The sterile barrier assembly of claim 21 wherein said balls comprise steel.

26. The sterile barrier assembly of claim 21 wherein one or more of said plurality of balls have optically transparent portions for transmitting data.

27. A method for coupling the first and second surgical components with the sterile barrier assembly of claim 1, said method comprising the steps of:
    placing the sterile barrier assembly on the first surgical component;
    placing the second surgical component on the sterile barrier assembly; and
    preloading a preloading element to kinematically couple the surgical components together through the sterile barrier assembly with the plurality of kinematic couplers.

28. A sterile barrier assembly for establishing a barrier between first and second surgical components, said sterile barrier assembly comprising:
    a protective covering including:
        an interface having a plurality of kinematic couplers integrated therein configured to provide a kinematic coupling between the first and second surgical components through said protective covering to constrain six degrees of freedom of movement between the surgical components, wherein each of said plurality of kinematic couplers are arranged to laterally move relative to one another; and
    a drape attachable to said interface.

29. A sterile barrier assembly for establishing a barrier between first and second surgical components, said sterile barrier assembly comprising:
    a protective covering including:
        an interface having a plurality of kinematic couplers integrated therein configured to provide a kinematic coupling between the first and second surgical components through said protective covering to constrain six degrees of freedom of movement between the surgical components, wherein said interface includes a preloading element for preloading the kinematic coupling between the surgical components; and
    a drape attachable to said interface.

30. A sterile barrier assembly for establishing a barrier between first and second surgical components, said sterile barrier assembly comprising:
    a protective covering including:
        an interface having a plurality of kinematic couplers integrated therein configured to provide a kinematic coupling between the first and second surgical components through said protective covering to constrain six degrees of freedom of movement between the surgical components; and
    a drape attachable to said interface and comprising a ring defining an opening for receiving said interface and a flaccid portion attached to said ring.

31. A sterile barrier assembly for establishing a barrier between first and second surgical components, the first surgical component comprising a first mounting portion and the second surgical component comprising a second mounting portion, said sterile barrier assembly comprising:
    a protective covering having a plurality of kinematic couplers configured to engage the mounting portions and to provide the kinematic coupling between the mounting portions through said protective covering to constrain six degrees of freedom of movement between the surgical components.

* * * * *